(12) United States Patent
Anand et al.

(10) Patent No.: US 12,234,203 B2
(45) Date of Patent: Feb. 25, 2025

(54) PROCESS FOR THE SYNTHESIS OF CANNABIDIOL AND INTERMEDIATES THEREOF

(71) Applicant: COUNCIL OF SCIENTIFIC AND INDUSTRIAL RESEARCH AN INDIAN REGISTERED BODY INCORPORATED UNDER THE REGN. OF THE SOC. ACT (ACT XXI OF 1860), New Delhi (IN)

(72) Inventors: Radhika Anand, Jammu Jammu Kashmir (IN); Sumit Sharma, Jammu Jammu Kashmir (IN); Pankaj Singh Cham, Jammu Jammu Kashmir (IN); Veeranjaneyulu Gannedi, Jammu Jammu Kashmir (IN); Mukesh Kumar, Jammu Jammu Kashmir (IN); Varun Pratap Singh, Jammu Jammu Kashmir (IN); Vishav Prakash Rahul, Jammu Jammu Kashmir (IN); Ram Asrey Vishwakarma, Jammu Jammu Kashmir (IN); Parvinder Pal Singh, Jammu Jammu Kashmir (IN)

(73) Assignee: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 671 days.

(21) Appl. No.: 17/594,448

(22) PCT Filed: Mar. 11, 2021

(86) PCT No.: PCT/IN2021/050242
§ 371 (c)(1),
(2) Date: Oct. 15, 2021

(87) PCT Pub. No.: WO2021/181420
PCT Pub. Date: Sep. 16, 2021

(65) Prior Publication Data
US 2022/0340507 A1 Oct. 27, 2022

(30) Foreign Application Priority Data
Mar. 12, 2020 (IN) .............. 202011010503

(51) Int. Cl.
C07C 29/00 (2006.01)
C07C 37/14 (2006.01)
(Continued)

(52) U.S. Cl.
CPC .............. *C07C 29/00* (2013.01); *C07C 37/14* (2013.01); *C07C 37/48* (2013.01); *C07C 41/01* (2013.01);
(Continued)

(58) Field of Classification Search
CPC ....... C07C 29/00; C07C 37/48; C07C 391/02; C07C 37/14
See application file for complete search history.

(56) References Cited

U.S. PATENT DOCUMENTS

2006/0194761 A1   8/2006  Gu
2017/0008868 A1   1/2017  Dialer et al.
(Continued)

FOREIGN PATENT DOCUMENTS

EP       2578561 A1      4/2013
WO   WO-2006053766 A1   5/2006
(Continued)

OTHER PUBLICATIONS

Ceccherelli, P., et al., trans 1,2-functionalizaitn of cycloalkenes using selenium intermediates, Tetrahedron Letters, vol. 30, No. 24, pp. 3175-3178 (Year: 1989).*
(Continued)

*Primary Examiner* — Yate' K Cutliff
(74) *Attorney, Agent, or Firm* — Schwegman Lundberg & Woessner, P.A.

(57) ABSTRACT

The present invention relates to process for the preparation of cannabidiol (A) from the coupling of (D) and (E) through the intermediates (C) and (D) starting from compound (B). The invention further relates to the novel compounds (B), (C), (D) and (E) and reagents used in this process. More specifically, this invention provides the manufacturing of Cannabidiol (A) in milligram to gram or kilogram scale.

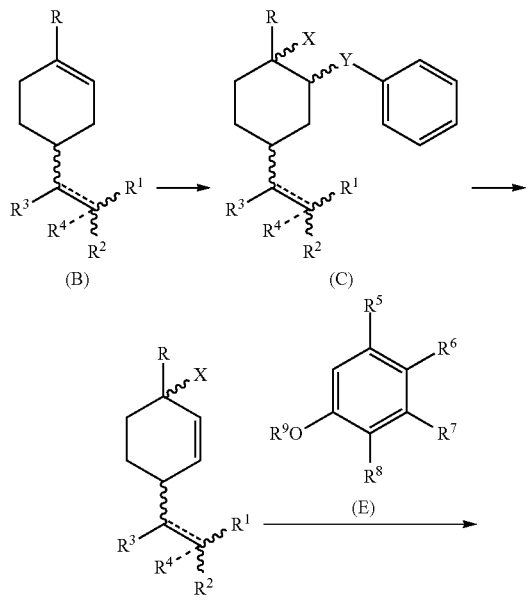

(Continued)

-continued

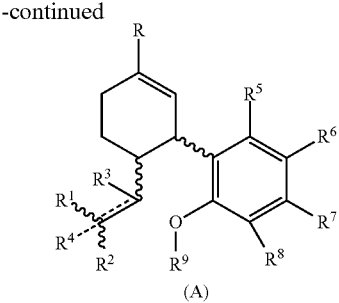

(A)

5 Claims, No Drawings

(51) Int. Cl.
- C07C 37/48 (2006.01)
- C07C 41/01 (2006.01)
- C07C 67/00 (2006.01)
- C07C 391/02 (2006.01)

(52) U.S. Cl.
CPC ............ *C07C 67/00* (2013.01); *C07C 391/02* (2013.01); *C07C 2601/10* (2017.05)

(56) References Cited

U.S. PATENT DOCUMENTS

| | | |
|---|---|---|
| 2017/0349518 A1 | 12/2017 | Dickman et al. |
| 2018/0319763 A1* | 11/2018 | Dialer .................. A61P 3/10 |

FOREIGN PATENT DOCUMENTS

| | | |
|---|---|---|
| WO | WO-2007041167 A3 | 11/2007 |
| WO | WO-2016135308 A1 | 9/2016 |
| WO | WO-2019033164 A1 | 2/2019 |
| WO | WO-2019046806 A1 | 3/2019 |
| WO | WO-2021181420 | 9/2021 |

OTHER PUBLICATIONS

Mori, K., Synthesie of 1S,4R0-4-isopropyl-1-methyl-2-cyclohexene-1-ol-, the aggregation pheromone of the ambrosia beetle Platypus quercivorus, its racemate, (1R,4R)-and (1S,4S)-isomers, Tetrahedron: Asymmetry, vol. 17, No. 14, pp. 2133-2142 (Year: 2006).*

"International Application No. PCT/IN2021/050242, International Search Report and Written Opinion mailed Sep. 7, 2021", (Sep. 7, 2021), 8 pgs.

Baek, Seung-Hwa, "Boron triflouride etherate on alimina—a modified Lewis acid reagent: an improved synthesis of cannabidiol", Tetrahedron Letters, vol. 26, Issue 8, 1985, pp. 1083-1086, (Jan. 2, 1985), 1083-1086.

Gerich, Mark E., et al., "Medical marijuana for digestive disorders: high time to prescribe?", American Journal of Gastroenterology: Feb. 2015—vol. 110—Issue 2—p. 208-214 // doi: 10.1038/ajg.2014.245, (Feb. 2015), 208-214.

Hawkes, Nigel, "Cannabis based drugs should be rescheduled to make research and prescribing easier, says chief medical officer", BMJ 2018;362:k2957 doi: 10.1136/bmj.k2957 (Published Jul. 5, 2018), (Jul. 5, 2018), 2 pgs.

Hosking, Richard, et al., "Cannabis in neurology—a potted review", Nature Reviews Neurology, vol. 10, (2014), (Jul. 8, 2014), 429-430.

Maroon, Joseph, et al., "Review of the neurological benefits of phytocannabinoids", Surgical Neurology International 2018, 9:91, (Apr. 26, 2018), 13 pgs.

Mechoulam, R., et al., "A Total Synthesis of dl -?1-Tetrahydrocannabinol, the Active Constituent of Hashish", J. Am. Chem. Soc., 87 (14) (1965), (Jul. 1, 1965), 3273-3275.

Mechoulam, Raphael, et al., "Recent advances in the chemistry and biochemistry of cannabis", Chem. Rev., 76(1) (1976), (Feb. 1, 1976), 75-112.

Ceccherelli, P., et al., "Trans 1,2-functionalization of cycloalkenes using selenium intermediates", Tetrahedron Letters; vol. 30, Issue 24, 1989, pp. 3175-3178; https://doi.org/10.1016/S0040-4039(00)99194-9, (Mar. 9, 2001), 3175-3178.

Fischer, James J., et al., "Nuclear Magnetic Relaxation Study of Intermolecular Complexes. The Mechanism of Penicillin Binding to Serum Albumin", J. Am. Chem. Soc. 1965, 87, 14, 3237-3244; https://doi.org/10.1021/ja01092a040, (Jul. 1, 1965), 3237-3244.

Mori, Kenji, "Synthesis of (1S,4R)-4-isopropyl-1-methyl-2-cyclohexen-1-ol, the aggregation pheromone of the ambrosia beetle Platypus quercivorus, its racemate, (1R,4R)- and (1S,4S)-isomers", Tetrahedron: Asymmetry; vol. 17, Issue 14, Aug. 28, 2006, pp. 2133-2142; https://doi.org/10.1016/j.tetasy.2006.07.030, (Aug. 22, 2006), 2133-2142.

Crombie, L., et al., "Synthesis of Cannabinoid Methyl Esters and Acids", ChemInform Abstract: Synthesis of Cannabinoid Methyl Esters and Acids; DOI 10.1002/chin.197738361; Sep. 1977; Chemischer Informationsdienst 1977, 8, No. 38, Abstract 361, (Sep. 1977), 3 pgs.

Gerich, Mark E., et al., "Medical marijuana for digestive disorders: high time to prescribe?", American Journal of Gastroenterology: Feb. 2015—vol. 110—Issue 2—p. 208-214 // doi: 10.1038/ajg.2014.245 [abstract only], (Feb. 2015), 208-214.

Gould, Julie, "The cannabis crop", Nature 525, S2-S3 (2015). https://doi.org/10.1038/525S2a, (Sep. 24, 2015), 2 pgs.

Grayson, Michelle, et al., "Cannabis", Nature 525, S1 (2015). https://doi.org/10.1038/525S1a, (Sep. 24, 2015), 1 pg.

Hanus, Lumir Ondrej, et al., "Phytocannabinoids: a unified critical inventory", Nat. Prod. Rep., vol. 33, No. 12 (2016), (Dec. 2016), 1357-1392.

Hosking, Richard, et al., "Cannabis in neurology—a potted review", Nature Reviews Neurology, vol. 10, pp. 429-430 (2014) [abstract only], (Jul. 8, 2014), 429-430.

Iseger, Tabitha A., et al., "A systematic review of the antipsychotic properties of cannabidiol in humans", Schizophrenia Research 162 (2015) 153-161, (Feb. 7, 2015), 153-161.

Marcu, Jahan P., "An Overview of Major and Minor Phytocannabinoids", Neuropathology of Drug Addictions and Substance Misuse, vol. 1, Chapter 62, (2016), 672-678.

Mechoulam, Raphael, et al., "Recent advances in the chemistry and biochemistry of cannabis", Chem. Rev., 76(1) (1976) [first page only], (Feb. 1, 1976), 75-112.

* cited by examiner

PROCESS FOR THE SYNTHESIS OF CANNABIDIOL AND INTERMEDIATES THEREOF

PRIORITY CLAIM TO RELATED APPLICATIONS

This application is a U.S. national stage filing under 35 U.S.C. § 371 from International Application No. PCT/IN2021/050242, filed on 11 Mar. 2021, and published as WO2021/181420 on 16 Sep. 2021, which claims the benefit under 35 U.S.C. 119 to India application No. 202011010503, filed on 12 Mar. 2020, the benefit of priority of each of which is claimed herein, and which applications and publication are hereby incorporated herein by reference in their entirety.

FIELD OF INVENTION

The present invention relates to process for the preparation of cannabidiol of formula (A) involving the coupling of compound of formula (D) and compound of formula (E) through the intermediates of formula (C) and formula (D) starting from compound of formula (B). The invention further relates to the novel compounds of formulae (B), (C), (D) and (E) and reagents used in this process. More specifically, this invention provides the process for the preparation of cannabidiol of formula (A) in milligram to gram or kilogram scale.

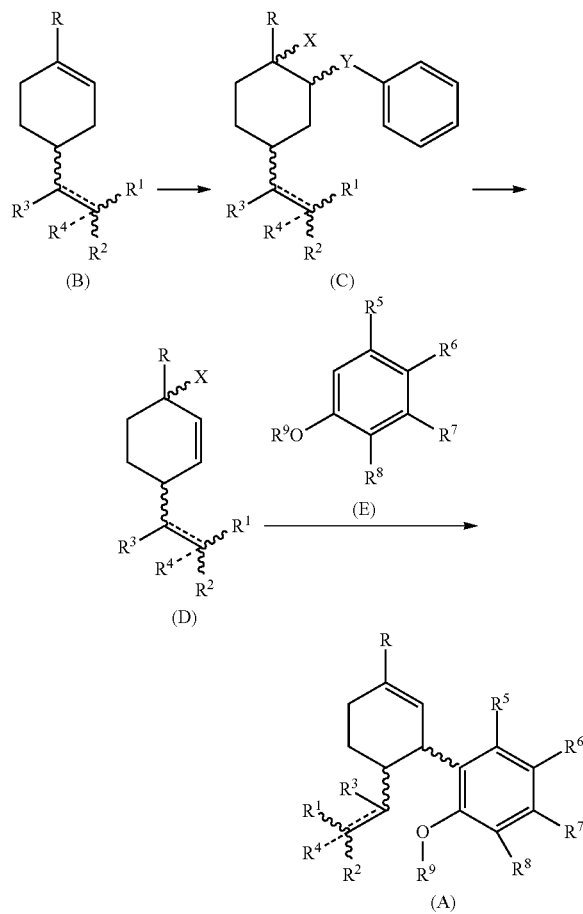

BACKGROUND OF THE INVENTION

Cannabis has been associated with Indian culture and medicine since ancient time; however, due to its abuse as psycho-active substance, it has been banned worldwide for decades and put under narcotic list in India also (J. Gould, Nature, 525, (2015), 52-53; M. Grayson, Nature outlook, 525, Issue no. 7570). Cannabis is well known for the occurrence of a unique class of terpenophenolic compounds named as phytocannabinoids. About 104 phytocannabinoids have been isolated from the plant till date (R. Mechaulam et. al., Chemical Reviews, 1976, 76); (L. O. Hanus et. al., Nat. Prod. Rep., 2016, 33, 1357); (J. P. Marcu, An Overview of Major and Minor Phytocannabinoids Chapter 62, 672-678). However, the major ones, as well as most studied and medicinally useful are $\Delta^9$-tetrahydrocannabinol (THC) and cannabidiol (CBD). CBD and THC are found throughout the seeds, stalk and flowers of cannabis plants, including hemp and marijuana varieties of cannabis. Scientific discoveries have confirmed that phytocannabinoids particularly $\Delta^9$-tetrahydrocannabinol (THC) and cannabidiol (CBD) isolated from cannabis sp., have several therapeutic indications (pain management including rheumatic, reduce nausea and vomiting, suppress seizure activity, combat anxiety, depression, psychosis disorders, anti-inflammatory properties, anti-tumoral properties and antioxidant properties that could fight neurodegenerative disorders) apart from psychoactive properties which come from THC (R. Hosking and J. Zajicek J. Nat. Rev. Neurol. 8 Jul. 2014; M. E. Gerich et al., Am J Gastroenterol, 9 Sep. 2014; Joseph Maroon 2018), however on the other hand, CBD is totally devoid of psycho-active properties (T. A. Iseger and M. G. Bossong, Schizophrenia Research 162, 153-161, 2015). In last decades, four drugs namely Nabiximols, Dronabinol, Nabilone and Cannabidiol has been approved by regulatory bodies; and many others, such as Ajulemic acid and Dexanabinol are under process of regulatory approval. Cannabidiol being non-psychotic is the first choice among academic and industrial researchers throughout the world (Hawkes 2018). In most of the CBD preparation available around the globe, isolation from a natural source is the best choice. However, its occurrence is highly varied among the accession and is influenced by number of factors. Considering the importance of cannabidiol, a synthetic approach could be a better opportunity, and number of researchers has developed many synthetic strategies. In this direction, the first total synthesis is developed by Mechoulam, and Gaoni (J Am Chem Soc 1965, 87, 3237-5) which involves the addition of 1,3-dimethoxy-olivetol to geranial followed by cyclization and demethylation leads to the formation of ($\pm$)-cannabidiol. In nature, cannabidiol is present as (−)-enantiomers and therefore stereo-selective route for its synthesis is required. To develop an stereo-selective approach, coupling of chiral terpenes were used as coupling partner and coupled with resorcinol derivative in the presence of number of Lewis-acids [Lukas Dialer et al., (US20170008868A1); Hong Gu et al., (US2006/0194761A1); Gutman, Arie et al., (WO 2006053766A1); Reekie, Tristan et al., (WO2019/033164A1); Bencivenga, Marc et al., (WO2019/046806); Burdick, David C et al., (EP2578561); Seung-Hwa Baek et al., Tetrahedron letters, 26, 1985, 1083-1086). These methods lead to the formation of cannabidiol with natural configuration but other phytocannabinoids were also being formed by either cyclization of products or coupling form other position.

In other attempts, the issue of selectivity was addressed by using substituted coupling partners. D. Burdick et al., (WO2007041167 A3) and D. Daniel et al., (US2017/0349518) coupled 6-carbethoxy olive oil with menthadienol in the presence of dimethylformamide and dineopentylacetal as a catalyst with improved selectivity with a yield of 42% of cannabidiol-carboxylic acid ethyl ester. In another route, Crombie et. al., (chemischer Informationsdienst 1977, 8, No. 38, Abstract 361) coupled olivetol carboxylic ester with unsaturated hydrocarbons, alcohols, ketones, or derivatives thereof which gave corresponding carboxylic acid ester of cannabinoids, which in final step underwent decarboxylation to furnish ester-free cannabinoids (J. Chem. Research 114, 1301-1345 1977). In another approach, Burdick, David C et al., (EP2578561A1) describes the synthesis of CBD from (+)-limonene oxide and dihalo-olivetol via the four-step sequences, epoxide opening and elimination of dimethyl-amino to menthadienol, condensation with olivetol derivative by using protic acid or Lewis acid, and reductive dehalogenation.

The low selectivity, cost, multi-steps, poor yields of previous methods demonstrates the manufacturing of cannabinoid compounds difficult. The cause of difficulties also includes the chromatographic purification and instability of cannabidiol, which leads to the formation of other related unwanted phytocannabinoids and their derivatives. The present invention relates to the process for the stereoselective preparation of cannabidiol and its related compounds starting from inexpensive starting material limonene and related compounds via three steps sequence difunctionalization, elimination and condensation.

OBJECTIVE OF THE INVENTION

The main objective of the present invention is to provide a stereoselective route for the production of (+) or (−) cannabidiol and related compounds thereof. The (+) or (−) cannabidiol and related compounds thereof can be prepared via three steps sequences di-functionalization of (+) or (−) limonene or limonene derivative thereof, elimination to (+) or (−) menthadienol or derivatives thereof, and metal triflate or acid or hetero-acids catalyzed condensation of (+) or (−) menthadienol or menthadienol derivatives with olivetol or olivetol derivatives thereof.

SUMMARY OF THE INVENTION

In an aspect of the present invention, there is provided a process for the preparation of cannabidiol of following formula (A) and intermediates thereof:

Scheme 1: General scheme for the preparation of cannabidiol and related compounds

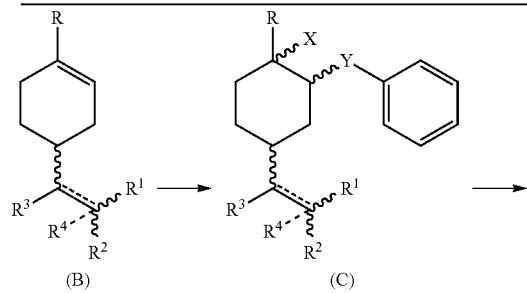

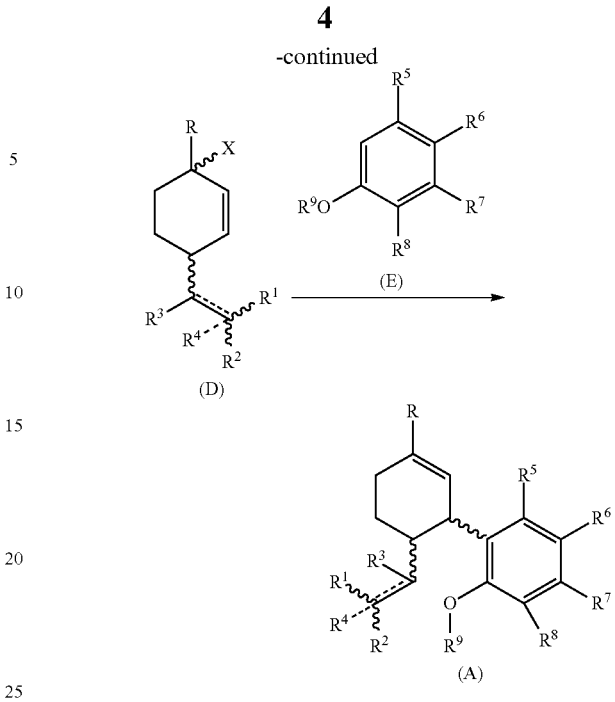

wherein R is independently selected from H, OH, alkyl, alkenyl, alkynyl, or cycloalkyl; $R_1$, $R_2$, $R_3$ and $R_4$ are independently selected from H, OH, alkyl, alkenyl, alkynyl, acyl, acyloxy, or cycloalkyl; X is independently selected from OH, H, heteroaryl, Cl, Br, I, OTf, OTs, or phosphinyl; Y is independently selected from S, SO, Se, SeO, Cl, Br, I, N-dialkyl, N-aryl, or N-heteroaryl; $R_5$, $R_6$, $R_7$, $R_8$, $R_9$ are independently selected from H, halogen, —CN, —NO$_2$, —OH, alkyl, —O-alkyl, —COOH, —C(O), —C alkyl, —C(O)OC, S-alkyl, —SO-alkyl, —SO$_2$-alkyl, S-aryl, —SO-aryl, —SO$_2$-aryl, SO-heteroaryl, —SO$_2$—N-aryl, —N—SO$_2$-aryl NR'R", alkenyl, alkynyl, acyl, acyloxy, aryl, heteroaryl, cycloalkyl, or heterocyclyl; wherein the alkyl or aryl or heteroaryl, optionally substituted with one or more substituents independently selected from the group consisting of halogen, OH, alkyl, —O-alkyl, —COOH, —C(O), —C alkyl, —C(O)OC, alkyl, NR'R", and —(CH$_2$)$_n$NR'R"; wherein each alkyl, alkenyl, alkynyl, cycloalkyl, acyl, acyloxy, aryl, arylalkyl, heteroaryl, or heterocyclyl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl, each optionally substituted with one or more substituents Q1; and (c) —C(O)R$^a$, —C(O)OR$^a$, —C(O)NR$^b$R$^c$, —C(N R$^a$) NR$^b$R$^c$, —OR$^a$, —OC(O) R$^a$, —OC(O)OR$^a$, OC(O)NRbRc, —OC(=N R$^a$)NR$^b$R$^c$, —OS(O) R$^a$, —OS(O)2R$^a$, —OS(O)NR$^b$R$^c$, —OS(O)2NR$^b$R$^c$, —NR$^b$R$^c$, —N R$^a$ C(O)R$^d$, —N R$^a$ C(O) OR$^d$, —N R$^a$ (O)NR$^b$R$^c$, —NR$^a$C(=NR$^d$)NR$^b$R$^c$, —N R$^a$ S(O)R$^d$, —N R$^a$ S(O)2R$^d$, —N R$^a$ S(O)NR$^b$R$^c$, —N R$^a$ S(O)$_2$NR$^b$R$^c$, —SR$^a$, —S(O) R$^a$, —S(O)$_2$R$^a$, —S(O)NR$^b$R$^c$, and —S(O)$_2$NR$^b$R$^c$, or —(CH$_2$)$_n$NR'R";

wherein R$^a$, R$^b$, R$^e$, and R$^d$ is independently selected from (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl, optionally substituted with one or more substituents Q$^1$; or (iii) R$^b$ and R$^c$ together with the N atom to which they are attached from heterocyclyl, optionally substituted with one or more substituents Q$^1$;

wherein Q$^1$ is independently selected from the group consisting of (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl; and (c) —C(O)R$^e$, —C(O)OR$^e$, —C(O)NR$^f$R$^g$, —C(N R$^e$) NR$^f$R$^g$, —OR$^e$, —OC(O) R$^e$, —OC(O)OR$^e$, OC(O)NR$^f$R$^g$, —OC(=N R$^e$)NRfRg, —OS(O) R$^e$, —OS(O)$_2$R$^e$, —OS(O)NR$^f$R$^g$, —OS(O)2NR$^f$R$^g$, —NR$^f$R$^g$, —N R$^e$ C(O)R$^h$, —N R$^e$ C(O)OR$^h$, —N R$^e$ (O)NR$^f$R$^g$, —NR$^e$C(=NR$^h$)NR$^f$R$^g$, —N R$^e$ S(O)R$^h$, —N R$^e$ S(O)$_2$R$^h$, —N R$^e$ S(O)NR$^f$R$^g$, —N R$^e$ S(O)$_2$NR$^f$R$^g$, —SR$^e$, —S(O) R$^e$, —S(O)$_2$R$^e$, —S(O)NR$^f$R$^g$, or —S(O)$_2$NR$^f$R$^g$;

wherein R$^e$, R$^f$, R$^g$, and R$^h$ is independently selected from (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl; (iii) R$^f$ and R$^g$ together with the N atom to which they are attached from heterocyclyl;

wherein each ------- represents a single or double bond;

provided that both ------- groups are not double bonds, and wherein denoted, dash marks indicate the points of attachment;

wherein, ∿∿ represents a single bond, above the plane or below the plane or both above the plane or both below the plane or one is above the plane and one is below the plane.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION OF THE INVENTION

The invention will now be described in detail in connection with certain preferred and optional embodiments, so that various aspects thereof may be more fully understood and appreciated.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "alkyl" refers to straight or branched aliphatic hydrocarbon groups having the specified number of carbon atoms, which are attached to the rest of the molecule by a single atom, which may be optionally substituted by one or more substituents. Preferred alkyl groups 1 to 6 carbon atoms include, without limitation, methyl, ethyl, n-propyl, isopropyl, butyl, isobutyl, t-butyl, pentyl, hexyl, and the like.

The term "aryl" refers to aromatic radicals having 6 to 14 carbon atoms, which may be optionally substituted by one or more substituents. Preferred aryl groups include, without limitation, phenyl, naphthyl, indanyl, biphenyl, and the like.

The term "arylalkyl" refers to an aryl group directly bonded to an alkyl group, which may be optionally substituted by one or more substituents and have 7 to 15 carbon atoms. Preferred arylalkyl groups include, without limitation, —$CH_2C_6H_5$, —$C_2H_4C_6H_5$, and the like. The terms arylalkyl and aralkyl may be used interchangeably.

The term "heterocyclyl" refers to a heterocyclic ring radical which may be optionally substituted by one or more substituents. The heterocyclyl ring radical may be attached to the main structure at any heteroatom or carbon atom that results in the creation of a stable structure.

Furthermore, the term "heterocyclyl" refers to a stable 3 to 15 membered rings radical, which consists of carbon atoms and from one to five heteroatoms selected from nitrogen, phosphorus, oxygen and sulfur. For purposes of this invention the heterocyclic ring radical may be monocyclic, bicyclic or tricyclic ring systems, and the nitrogen, phosphorus, carbon, or sulfur atoms in the heterocyclic ring radical may be optionally oxidized to various oxidation states.

The term "heteroaryl" refers to an aromatic heterocyclic ring radical as defined above. The heteroaryl ring radical may be attached to the main structure at any heteroatom or carbon atom that results in the creation of stable structure.

The term "fused heterocyclyl" refers to monocyclic or polycyclic ring, polycyclic ring system refers to a ring system containing 2 or more rings, preferably bicyclic or tricyclic rings, in which rings can be fused, bridged or spiro rings or any combinations thereof. A fused ring as used herein means that the two rings are linked to each other through two adjacent ring atoms common to both rings. The fused ring can contain 1-4 hetero atoms independently selected from N, O, and S. The rings can be either fused by nitrogen or —CH— group.

The term "cycloalkyl" refers to non-aromatic mono or polycyclic ring system of about 3 to 7 carbon atoms, which may be optionally substituted by one or more substituents. The polycyclic ring denotes hydrocarbon systems containing two or more ring systems with one or more ring carbon atoms in common i.e. a spiro, fused or bridged structures. Preferred cycloalkyl groups include, without limitation, cyclopropyl, cyclobutyl, cyclopentyl, cyclohexyl, and the like.

The term "alkenyl" refers to an aliphatic hydrocarbon group containing a carbon-carbon double bond, and which may be straight or branched chain having about 2 to 6 carbon atoms, which may be optionally substituted by one or more substituents. Preferred alkenyl groups include, without limitation, ethenyl, 1-propenyl, 2-propenyl, iso-propenyl, 2-methyl-1-propenyl, 1-butenyl, 2-butenyl and the like.

The term "alkynyl" refers to a straight or branched hydrocarbyl radicals having at least one carbon-carbon triple bond and having in the range of 2-6 carbon atoms, which may be optionally substituted by one or more substituents. Preferred alkynyl groups include, without limitation, ethynyl, propynyl, butynyl and the like.

The term "acyl" refers to a group derived by the removal of one or more hydroxyl groups from an oxoacid, including inorganic acids and it has a double-bonded oxygen atom and R group (R—C=O). R group of the acyl includes but not limited to alkyl, alkenyl, alkynyl, aryl, cycloalkyl, haloalkyl, arylalkyl, heteroaryl, heterocyclyl and the like.

The term "acyloxy" refers to the acyl group bonded to oxygen: R—C(=O)—O— wherein R—C(=O) is the acyl group. R group includes but not limited to alkyl, alkenyl, alkynyl, aryl, cycloalkyl, haloalkyl, arylalkyl, heteroaryl, heterocyclyl and the like.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature in the range of −40° C. to 60° C. should be interpreted to include not only the explicitly recited limits of −40° C. to 60° C. but also to include sub-ranges, such as −30° C. to 50° C., −10° C. to 40° C., 0° C. to 35° C. and so forth, as well as individual amounts, within the specified ranges, such as 19.6° C., and 27.3° C.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a process for the preparation of the compound of Formula (A)

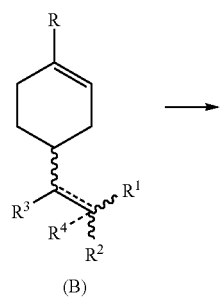

(B)

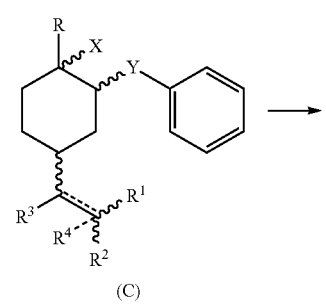

(C)

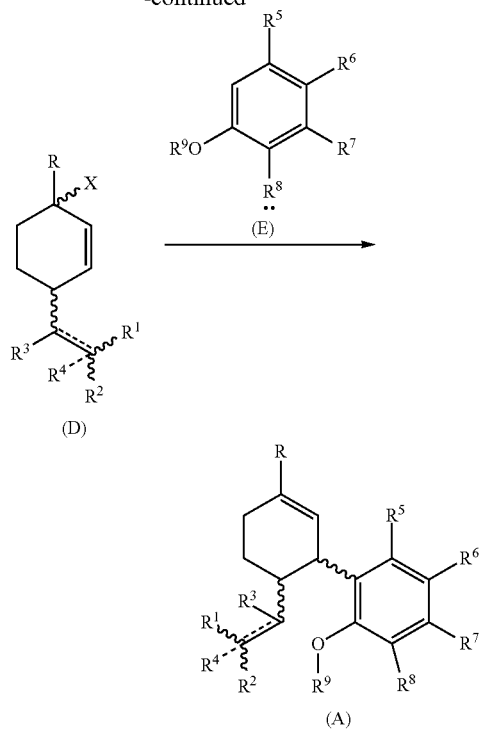

wherein R is independently selected from H, OH, alkyl, alkenyl, alkynyl, or cycloalkyl; $R_1$, $R_2$, $R_3$ and $R_4$ are independently selected from H, OH, alkyl, alkenyl, alkynyl, acyl, acyloxy, or cycloalkyl; X is independently selected from OH, H, heteroaryl, Cl, Br, I, OTf, OTs, or phosphinyl; Y is independently selected from S, SO, Se, SeO, Cl, Br, I, N-dialkyl, N-aryl, or N-heteroaryl; $R_5$, $R_6$, $R_7$, $R_8$, $R_9$ are independently selected from H, halogen, —CN, —NO$_2$, —OH, alkyl, —O-alkyl, —COOH, —C(O), —C alkyl, —C(O)OC, S-alkyl, —SO-alkyl, —SO$_2$-alkyl, S-aryl, —SO-aryl, —SO$_2$-aryl, SO-heteroaryl, —SO$_2$—N-aryl, —N—SO$_2$-aryl NR'R", alkenyl, alkynyl, acyl, acyloxy, aryl, heteroaryl, cycloalkyl, or heterocyclyl; wherein the alkyl, aryl or heteroaryl, are optionally substituted with one or more substituents independently selected from the group consisting of halogen, OH, alkyl, —O-alkyl, —COOH, —C(O), —C alkyl, —C(O)OC, alkyl, NR'R", and —(CH$_2$)$_n$NR'R"; wherein the alkyl, alkenyl, alkynyl, cycloalkyl, acyl, acyloxy, aryl, arylalkyl, heteroaryl, or heterocyclyl is optionally substituted with one or more groups, each independently selected from (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ arylalkyl, heteroaryl, or heterocyclyl, each optionally substituted with one or more in one embodiment, one, two, three, or four substituents $Q^1$; and (c) —C(O)R$^a$, —C(O)OR$^a$, —C(O)NR$^b$R$^c$, —C(N R$^a$) NR$^b$R$^c$, —OR$^a$, —OC(O) R$^a$, —OC(O)OR$^a$, OC(O)NR$^b$R$^c$, —OC(=N R$^a$)NR$^b$R$^c$, —OS(O)R$^a$, —OS(O)2R$^a$, —OS(O)NR$^b$R$^c$, —OS(O)2NR$^b$R$^c$, —NR$^b$R$^c$, —NR$^a$C(O)R$^d$, —N R$^a$ C(O)OR$^d$, —NR$^a$(O)NR$^b$R$^c$, —NR$^a$C(=NR$^d$)NR$^b$R$^c$, —N R$^a$S(O)R$^d$, —NR$^a$S(O)2R$^d$, —NR$^a$S(O)NR$^b$R$^c$, —NR$^a$ S(O)$_2$NR$^b$R$^c$, —SR$^a$, —S(O)R$^a$, —S(O)$_2$R$^a$, —S(O)NR$^b$R$^c$, —S(O)$_2$NR$^b$R$^c$, or —(CH$_2$)$_n$NR'R"; wherein, R$^a$, R$^b$, R$^e$, and R$^d$ are independently selected from (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl, each optionally substituted with one or more substituents $Q^1$; or (iii) R$^b$ and $R^c$ together with the N atom to which they are attached from heterocyclyl, optionally substituted with one or more substituents $Q^1$; wherein, $Q^1$ is independently selected from the group consisting of (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, and heterocyclyl; and (c) —C(O) $R^e$, —C(O)OR$^e$, —C(O)NR$^f$R$^g$, —C(NR$^e$) NR$^f$R$^g$, —OR$^e$, —OC(O) R$^e$, —OC(O)OR$^e$, OC(O)NR$^f$R$^g$, —OC(=NR$^e$) NR$^f$R$^g$, —OS(O) R$^e$, —OS(O)$_2$R$^e$, —OS(O)NR$^f$R$^g$, —OS (O)2NR$^f$R$^g$, —NR$^f$R$^g$, —N R$^e$C(O)R$^h$, —N R$^e$C(O)OR$^h$, —N R$^e$(O)NR$^f$R$^g$, —NR$^e$C(=NR$^h$)NR$^f$R$^g$, —N R$^e$ S(O)R$^h$, —N R$^e$ S(O)$_2$R$^h$, —N R$^e$ S(O)NR$^f$R$^g$, —N R$^e$ S(O)$_2$NR$^f$R$^g$, —SR$^e$, —S(O) R$^e$, —S(O)$_2$R$^e$, —S(O)NR$^f$R$^g$, or —S(O)$_2$NR$^f$R$^g$; wherein R$^e$, R$^f$, R$^g$, and R$^h$ is independently selected from (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$arylalkyl, heteroaryl, or heterocyclyl; (iii) R$^f$ and R$^g$ together with the N atom to which they are attached from heterocyclyl; wherein, each ------- represents a single or double bond; provided that both ------- groups are not double bonds, and wherein denoted, dash marks indicate the points of attachment; wherein, ∿∿∿ represents a single bond, above the plane or below the plane or both above the plane or both below the plane or one is above the plane and one is below the plane.

In an embodiment of the present invention there is provided the process as disclosed herein, wherein the compounds are selected from a) (+)-1-methyl-2-(phenylselanyl)-4-(prop-1-en-2-yl)cyclohexan-1-ol
b) (−)-1-methyl-2-(phenylselanyl)-4-(prop-1-en-2-yl)cyclohexan-1-ol
c) 4-(2-hydroxypropan-2-yl)-1-methyl-2-(phenylselanyl)cyclohexan-1-ol
d) (+)-2-(4-hydroxy-4-methyl-3-(phenylselanyl)cyclohexyl)propan-2-yl 2,2,2-trifluoroacetate
e) 4-isopropyl-1-methyl-2-(phenylselanyl)cyclohexan-1-ol
f) (+)-1-methyl-4-(prop-1-en-2-yl)cyclohex-2-en-1-ol
g) (+)-1-methyl-2-(phenylselanyl)-4-(prop-1-en-2-yl)cyclohexan-1-ol (D2)
h) (+)-2-(4-hydroxy-4-methylcyclohex-2-en-1-yl)propan-2-yl 2,2,2-trifluoroacetate
i) (+)-4-isopropyl-1-methylcyclohex-2-en-1-ol
j) (−)-5'-methyl-4-pentyl-2'-(prop-1-en-2-yl)-1',2',3',4'-tetrahydro-[1,1'-biphenyl]-2,6-diol
k) (+Z)-5'-methyl-4-pentyl-2'-(prop-1-en-2-yl)-1',2',3',4'-tetrahydro-[1,1'-biphenyl]-2,6-diol
l) (−)-2-((1R,2R)-2',6'-dihydroxy-5-methyl-4'-pentyl-1,2,3,4-tetrahydro-[1,1'-biphenyl]-2-yl)propan-2-yl 2,2,2-trifluoroacetate
m) (−)-(1'S,2'S)-2'-isopropyl-5'-methyl-4-pentyl-1',2',3',4'-tetrahydro-[1,1'-biphenyl]-2,6-diol
n) (−)-5'-methyl-2'-(prop-1-en-2-yl)-4-propoxy-1',2',3',4'-tetrahydro-[1,1'-biphenyl]-2,6-diol
o) (−)-4-(dodecyloxy)-5'-methyl-2'-(prop-1-en-2-yl)-1',2',3', 4'-tetrahydro-[1,1-biphenyl]-2,6-diol
p) (−)-4,5'-dimethyl-2'-(prop-1-en-2-yl)-1',2',3',4'-tetrahydro-[1,1'-biphenyl]-2,6-diol In an embodiment of the present invention, there is provided a process for the preparation of compound of formula (A) by coupling of compounds of formula (D) and compound of formula (E):

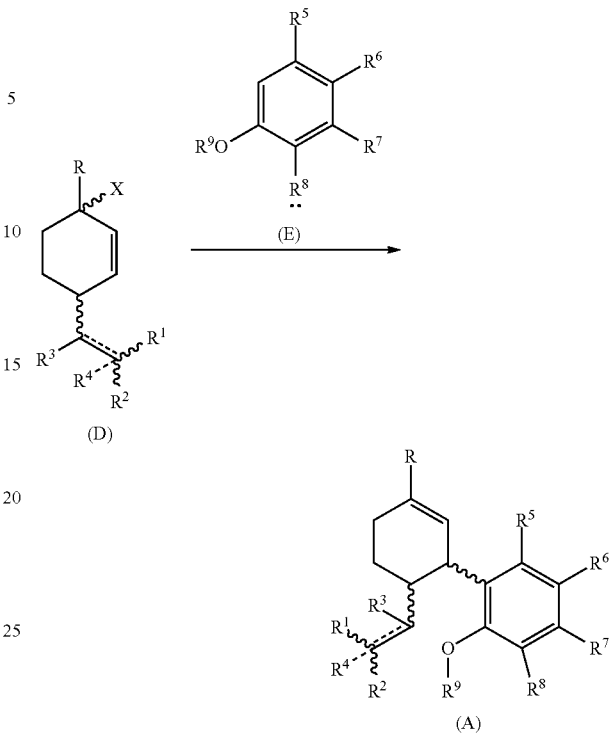

wherein the coupling reaction occurs with metal triflates selected from AgOTf, Ni(OTf)$_2$, Hg(OTf)$_2$, LiOTf, Bi(OTf)$_3$, Ln(OTf)$_3$, or Ac(OTf)$_x$, preferably AgOTf or along with ligands selected from bipyridyl, substituted bipyridyl phenanthrolene, substituted phenanthrolene, pyridine, substituted pyridine, BINAP, QINAP, PINAP, Ph$_3$P or like phosphines or with heterogeneous acids selected from mixed metal oxides, SiO$_2$—SO$_3$H/COFe$_2$O$_4$, SiO$_2$—Pr—SO$_3$H, zeolites, zeotype materials, OMR-[C4HMTA] [SO$_3$H], MPD-SO$_3$H-IL, MeAPSO, MeAPO, SAPO, ALPO$_4$, Natrolite, ZSM-5, H-ZSM-5, periodic mesoporous organosilicas (PMOs), mesoporous silicas (PMSs), H$_3$PW$_{12}$O$_{40}$, H$_4$SiW$_{12}$O$_{40}$, Cs$_2$HPW$_{12}$O$_{40}$, HPW/ZrO$_2$, HPW/Nb$_2$O$_5$, Montmorillonite, pyrophyllite, Talc, Vermiculite, Sauconite, Saponite, Nontronite, Kaolinite, Chlorite, Illite, SAPO-34, Zirconium phosphates or sulphates, cation/anion exchange resins amberlyst, amberlite, preferably montmorillonite clay; the coupling reaction is carried out in the presence of a solvent or mixture of solvents selected from tetrahydrofuran, dioxane, acetonitrile, chlorobenzene, dichloroethane, acetone, hexane, dichloromethane, chloroform, ethyl acetate, or toluene, preferably dichloroethane; and the coupling reaction is carried out with stirring the reaction mixture for time period in the range of 0.1 to 48 hours at a temperature in the range of −40° C. to 60° C.

In an embodiment of the present invention, there is provided a process for the preparation of compound of formula (A) by coupling of compounds of formula (D) and compound of formula (E) as disclosed herein, wherein the coupling reaction can occur alone with metal triflates (AgOTf, Ni(OTf)$_2$, Hg(OTf)$_2$, LiOTf, Bi(OTf)$_3$, Ln(OTf)$_3$, or Ac(OTf)$_x$) preferably AgOTf, or along with ligands selected from bipyridyl, substituted bipyridyl phenanthrolene, substituted phenanthrolene, pyridine, substituted pyridine, BINAP, QINAP, PINAP, Ph$_3$P or like phosphines or with heterogeneous acids, mixed metal oxides, SiO$_2$—SO$_3$H/COFe$_2$O$_4$, SiO$_2$—Pr—SO$_3$H, Zeolites, zeotype materials (OMR-[C4HMTA][SO$_3$H], MPD-SO$_3$H-IL, MeAPSO, MeAPO, SAPO, ALPO$_4$, Natrolite, ZSM-5, H-ZSM-5, periodic mesoporous organosilicas (PMOs), mesoporous silicas (PMSs), H$_3$PW$_{12}$O$_{40}$, H$_4$SiW$_{12}$O$_{40}$, Cs$_2$HPW$_{12}$O$_{40}$, HPW/ZrO$_2$, HPW/Nb$_2$O$_5$), Mantmorillonite, pyrophyllite, Talc, Vermiculite, Sauconite, Saponite, Nontronite, Kaolinite, Chlorite, Illite, SAPO-34, Zirconium phosphates or sulphates, cation/anion exchange resins amberlyst, or amberlite, preferably montmorillonite clay.

In an embodiment of the present invention, there is provided a process for the preparation of compound of formula (A) by coupling of compounds of formula (D) and compound of formula (E) as disclosed herein, wherein the coupling reaction occur in a solvent or mixture of solvents selected from tetrahydrofuran, dioxane, acetonitrile, chlorobenzene, dichloroethane, acetone, Hexane, dichloromethane, chloroform, ethyl acetate, or toluene, and the like, preferably dichloroethane.

In an embodiment of the present invention, there is provided a process for the preparation of compound of formula (A) by coupling of compounds of formula (D) and compound of formula (E) as disclosed herein, wherein the coupling reaction is carried out with stirring the reaction mixture for time period in the range of 0.1 to 48 hours. In another embodiment of the present invention, there is provided a process as disclosed herein wherein the coupling reaction is carried out with stirring the reaction mixture for time period in the range of 1 to about 3 hours, or about 6 to about 48 hours, or about 12 to about 24 hours, or about 14 to about 18 hours, preferably for 5-10 h.

In an embodiment of the present invention, there is provided a process for the preparation of compound of formula (A) by coupling of compounds of formula (D) and compound of formula (E) as disclosed herein, wherein the coupling reaction is carried out at a temperature in the range of −40° C. to 60° C. In another embodiment of the present invention, there is provided a process for the preparation of compound of formula (A) by coupling of compounds of formula (D) and compound of formula (E) as disclosed herein, wherein the coupling reaction is carried out at a temperature in the range of −40° C. to 40° C., or −35° C. to −25° C., or −0° C. to 50° C., preferably at 10° C. to 35° C.

In an embodiment of the present invention, there is provided a process for the preparation of compound of formula (D) from compound of formula (C) comprising the steps of:

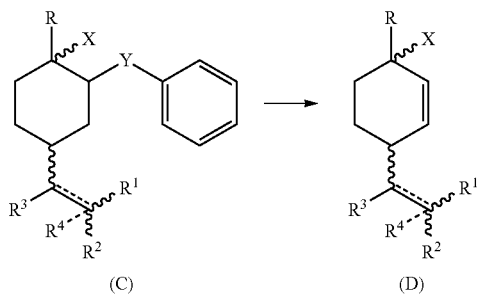

(C) → (D)

regenerating of double bond by elimination of group (Y) of compound formula (C) and conversion to compound formula (D) in the presence of oxidants selected from mCPBA, Oxone, DDQ, CAN, N-hydroxy succinamide, t-Butylhydroperoxide, Selectfluor, Hydrogen peroxide, BIAB, NFSI, TMSOTf, PyF-BF$_4$, PyF-OTf, TMPyF-OTf, or PIFA, preferably Selectfluor, and Hydrogen peroxide.

In an embodiment of the present invention, there is provided a process for the preparation of compound of formula (D) from compound of formula (C) as disclosed herein, wherein elimination is carried out in the presence of a solvent or a mixture of solvents, selected from H$_2$O, tetrahydrofuran, dioxane, acetonitrile, chlorobenzene, dichloroethane, acetone, hexane, dichloromethane, chloroform, ethyl acetate, or toluene, and the like.

In an embodiment of the present invention, there is provided a process for the preparation of compound of formula (D) from compound of formula (C) as disclosed herein, wherein regenerating of double bond by elimination is carried out by stirring the reaction mixture for a time period in the range of 0.1 to 48 hours. In another embodiment of the present invention, there is provided a process for the preparation of compound of formula (D) from compound of formula (C) as disclosed herein, wherein regenerating of double bond by elimination is carried out by stirring the reaction mixture for a time period in the range of 1 to 3 hours, or 6 to 48 hours, or 12 to 24 hours, or 14 to 18 hours.

In an embodiment of the present invention, there is provided a process for the preparation of compound of formula (D) from compound of formula (C) as disclosed herein, wherein regenerating of double bond by elimination is carried out at a temperature in the range of −40° C. to 60° C. In another embodiment of the present invention, there is provided a process for the preparation of compound of formula (D) from compound of formula (C) as disclosed herein, wherein regenerating of double bond by elimination is carried out at a temperature in the range of −40° C. to 40° C., or −35° C. to −25° C., or −0° C. to 5, preferably at −10° C. to 35° C.

In an embodiment of the present invention there is provided process for the preparation of compound of formula (C) by the bi-functionalization of double bond of compound of formula (B):

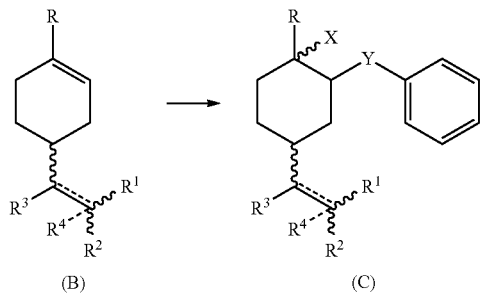

(B) → (C)

wherein the bi-functionalization of double bond is carried out in the presence of by a reagent selected from PhSeSePh, ZPhSeSePhZ, HetArSeSeHetAr, PhSSPh, ZPhSSPhZ, HetArSSHetAr, PhSeBr, ZPhSeBr HetArSeBr, PhSeCl, ZPhSeCl, HetArSeCl, PhSCl, ZPhSCl, HetArSCl, PhSBr, ZPhSBr HetArSBr, NBS, NIS, or NCS, along with oxidants or without oxidants, for example mCPBA, Oxone, DDQ, CAN, N-Hydroxy succinamide, t-Butylhydroperoxide, Selectfluor, Hydrogen peroxide, BIAB, NFSI, TMSOTf, PyF-BF$_4$, PyF-OTf, TMPyF-OTf preferably with PhSeBr, PhSeCl, PhSCl, PhSBr, PhSSPh/AgOTf, PhSSPh/Selectfluor, PhSeSePh/AgOTf, PhSeSePh/Selectfluor, or the like and wherein Z is independently halogen, —CN, —N(Me)$_2$, —NO$_2$, —OH, alkyl, —O-alkyl, —COOH, —C(O), —C alkyl.

In an embodiment of the present invention there is provided process for the preparation of compound of formula (C) by the bi-functionalization of double bond of compound of formula (B) as disclosed herein, wherein the bi-functionalization is carried out in the presence of a solvent or a mixture of solvents, selected from $H_2O$, tetrahydrofuran, dioxane, acetonitrile, chlorobenzene, dichloroethane, acetone, hexane, dichloromethane, chloroform, ethyl acetate, or toluene, and the like.

In an embodiment of the present invention there is provided process for the preparation of compound of formula (C) by the bi-functionalization of double bond of compound of formula (B) as disclosed herein, wherein the bi-functionalization is carried out by stirring the reaction mixture for a time period in the range of 0.1 h-48 h. In another embodiment of the present invention there is provided process for the preparation of compound of formula (C) by the bi-functionalization of double bond of compound of formula (B) as disclosed herein, wherein the bi-functionalization is carried out by stirring the reaction mixture for a time period in the range of 1 to 3 hours, or 6 to 48 hours, or 12 to 24 hours, or 14 to 18 hours, preferably 12-24 h.

In an embodiment of the present invention there is provided process for the preparation of compound of formula (C) by the bi-functionalization of double bond of compound of formula (B) as disclosed herein, wherein the bi-functionalization is carried out at a temperature in the range of −80° C. to 60° C., preferably −40° C. to −10° C.

In an embodiment of the present invention, there is provided a process for the preparation of compound of formula (A) by coupling of compound of formula (D) and compound of formula (E):

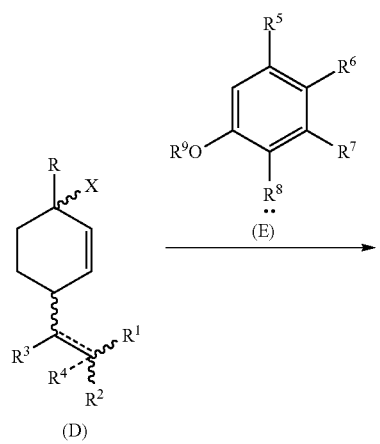

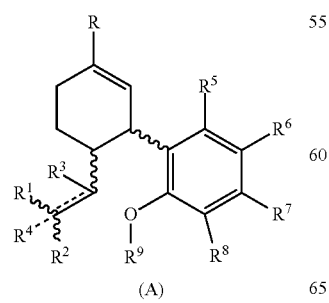

In an embodiment of the present invention, there is provided a process for the preparation of compound of formula (D) from compound of formula (C):

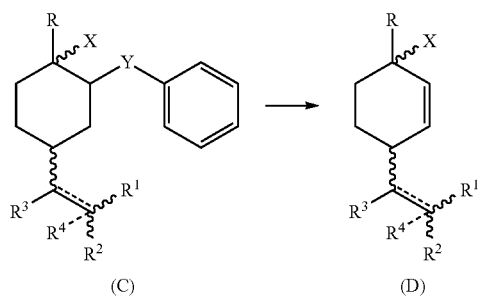

In an embodiment the present invention, there is provided a process for the preparation of compound of formula (C) by the bi-functionalization of double bond of compound of formula (B):

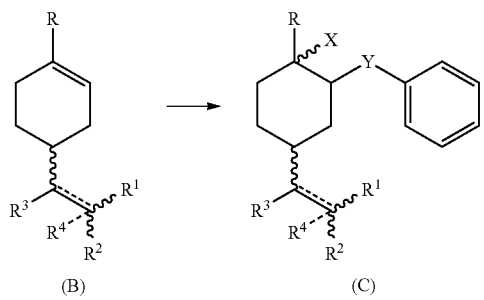

In an embodiment of the present invention, there is provided a compound of formula (C):

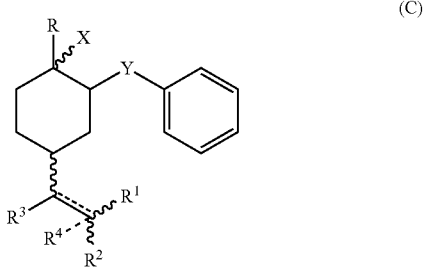

In an embodiment of the present invention, there is provided a compound of following formula (D):

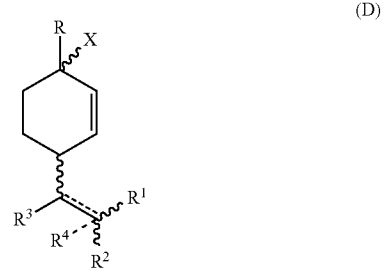

In an embodiment of the present invention, there is provided a compound of following formula (A):

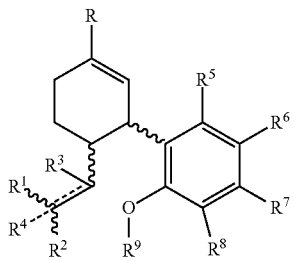
(A)

In an embodiment of the present invention, there is provided a compound of following formula (C):

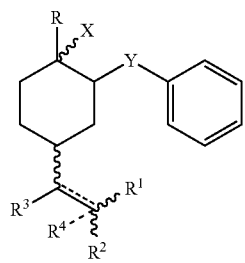
(C)

In an embodiment of the present invention, there is provided a compound of following formula (D):

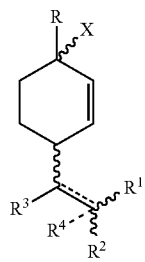
(D)

In an embodiment of the present invention, there is provided a compound of following formula (A):

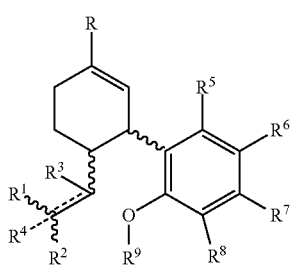
(A)

In an embodiment of the present invention, there is provided a compounds of following formula:

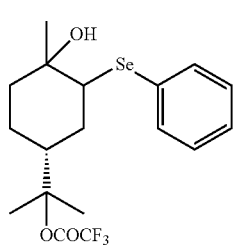
(+)-C4

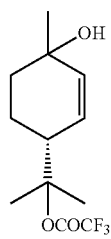
(+)-D3

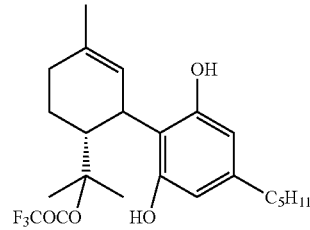
(-)-A3

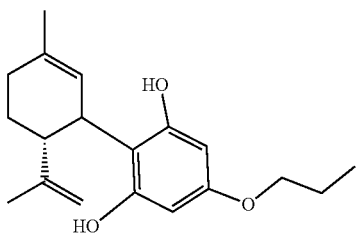
(-)-A5

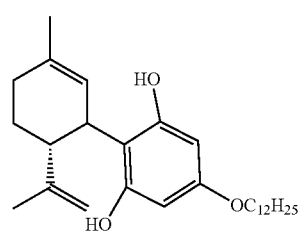
(-)-A6

List of Abbreviations

THC—Tetrahydrocannabinol
CBD—Cannabidiol
BINAP—(2,2'-bis(diphenylphosphino)-1,1'-binaphthyl)
DCE—Dichloroethane
m-CPBA—meta chloroperbenzoic acid
DDQ—2,3-Dichloro-5,6-dicyano-1,4-benzoquinone
CAN—Cerric ammonium nitrate
BIAB—(Diacetoxyiodo)benzene
NFSI—N-Fluorobenzenesulfonimide
OTf—trifluoromethanesulfonate
$CDCl_3$—Deuterated chloroform CD₃OD—Deuterated methanol
NMR—Nuclear Magnetic Resonance
PPM—Parts Per Million
TLC—Thin Layer Chromatography
HRMS—High Resolution Mass Spectrometry
THF—Tetrahydrofuran
DCM—Dichloromethane
ACN—Acetonitrile
DEPT—Distortionless Enhancement of Polarization Transfer
UV—Ultraviolet
ESI-MS—Electrospray ionization mass specrometry
LC-MS—Liquid chromatography-mass spectrometry
MS—Mass Spectrometry
MHz—Megahertz
TOF—Turnover Frequency
OCOCF₃—Trifluoroacetoxy
EtOAc—Ethyl acetate
AgOTf—Silver Trifluoromethanesulfonate
ESI—Electrospray ionisation
Ni(OTf)₂—Nickel (II) trifluoromethanesulfonate
Hg(OTf)₂—Mercury triflate
LiOTf—Lithium trifluoromethanesulfonate
Bi(OTf)₂—Bismuth(III) trifluoromethanesulfonate
Ln(OTf)₂—Lanthanide trifluoromethanesulfonate
Ac(OTf)₂—Actanide trifluoromethanesulfonate
PMO—Polarized Molecular Orbital
ZSM—Zeolite Socony Mobil-5
SAPO—Silicoaluminophosphate
PyF-BF₄—N-Fluoropyridinium triflate
TMSOTf—Trimethylsilyl trifluoromethanesulfonate
NBS—N—Bromosuccinimide
NIS—N—Iodosuccinimide
NCS—N—Chlorosuccinimide
Selectfluor-N-Chloromethyl-N'-fluorotriethylenediammonium bis(tetrafluoroborate)

Material and Method Used in Experiments:

All the product mixtures were analysed by thin layer chromatography. UV inactive compounds were visualized in staining solution and UV active compounds were detected with UV lamp (λ=254 nm). All the reactions were performed under inert atmosphere wherever required. Anhydrous solvents like THF, toluene, dichloroethane were dried in standard way. NMR spectra (¹HNMR, ¹³C, DEPT) were recorded in 400 MHz spectrometer using CDCl₃ and CD₃OD solvent. ESI-MS and HRMS spectra were recorded on LC-MS/MS and HRMS-6540-UHD machines. Optical rotations were measured on a Perkin Elmer polarimeter. Column chromatography was carried out with silica gel (60-120, 230-400 mesh)

EXAMPLES

The present invention is further defined in the following Examples. It should be understood that these Examples, while indicating preferred embodiments of the invention, are given by way of illustration only.

Step 1: Bi-Functionalization of (+) or (−) Limonene or Limonene Derivatives

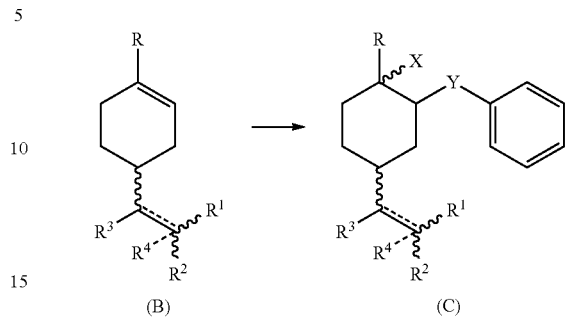

Preparation of (+)-1-methyl-2-(phenylselanyl)-4-(prop-1-en-2-yl)cyclohexan-1-ol (C1)

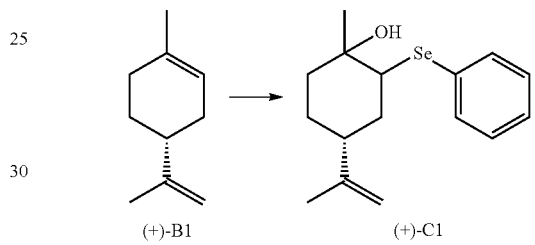

Example 1: To a stirred solution of (R)-(+)-limonene (B1) (1.2 g, 7.0 mmol) in ACN:H₂O (98:2, 6 ml) at −30 to −35° C. was added a solution of phenylselenyl bromide (1 g, 4.5 mmol) in ACN and allowed to stir at the same temperature. After the initiation of reaction, hydrogen peroxide (2.1 mmol) as an activator was added to the reaction mixture The progress of the reaction was monitored by TLC. After completion of the reaction (approximately 24 h), the reaction mixture was poured in hypo solution and extracted with ethyl acetate (3 times). The organic layer was dried over Na₂SO₄ and concentrated in vacuum. The crude material was subjected to silica gel column chromatography $R_f$=0.4 EtOAc:Hexane (0.3-9.7) as an eluent to afford the title compound (+) 1-methyl-2-(phenylselanyl)-4-(prop-1-en-2-yl)cyclohexan-1-ol (C1) (638 mg, 49%) as a yellow oil. ¹H NMR (400 MHz, CDCl₃): δ(ppm)=7.58 (dd, J=4 Hz, 2H), 7.27 (m, 3H), 4.71 (d, J=13.6 Hz, 2H), 3.44 (t, J=4 Hz, 1H), 2.33 (m, 1H), 2.21 (m, 1H), 1.85 (m, 2H), 1.68 (s, 3H), 1.64 (m, 3H), 1.41 (s, 3H), 1.26 (bs, 1H); ¹³C NMR (100 MHz, CDCl₃): δ(ppm)=149.03, 134.41, 130.55, 129.13, 127.39, 109.29, 72.59, 54.62, 39.54, 35.24, 33.70, 29.55, 26.24, 21.35; $[α]_D^{20}$=+129 (c=1.0, CHCl₃); LC-MS: (ESI+): m/z calcd for C₁₆H₂₂OSe 310.084; found 327.25.

TABLE 1

Reaction conditions for synthesis of compound formula (+)-C1 from R-(+)-B1

| EXAMPLE | REACTANT | REAGENTS AND CONDITIONS | YIELD (%) |
|---|---|---|---|
| 2 | R-(+)-B1 | PhSeSePh, Oxone, ACN:H₂O, rt, 7-8 h | (+)-C1 (24%) |

TABLE 1-continued

Reaction conditions for synthesis of
compound formula (+)-C1 from R-(+)-B1

| EXAMPLE | REACTANT | REAGENTS AND CONDITIONS | YIELD (%) |
|---|---|---|---|
| 3 | R-(+)-B1 | PhSeSePh, DDQ, ACN:H$_2$O, rt, 7-8 h | (+)-C1 (12%) |
| 4 | R-(+)-B1 | PhSeSePh, tBuOOH, ACN:H$_2$O, rt, 7-8 h | (+)-C1 (8%) |
| 5 | R-(+)-B1 | PhSeSePh, Selectfluor, ACN:H$_2$O, rt, 7-8 h | (+)-C1 (34%) |
| 6 | R-(+)-B1 | PhSeSePh, Selectfluor, ACN:H$_2$O, 0°, 7-8 h | — |
| 7 | R-(+)-B1 | PhSeSePh, Selectfluor, ACN:H$_2$O, 10°, 7-8 h | — |
| 8 | R-(+)-B1 | PhSeSePh, Selectfluor, DCM:H$_2$O, rt, 7-8 h | (+)-C1 (18%) |
| 9 | R-(+)-B1 | PhSeSePh, Selectfluor, Acetone:H$_2$O, rt, 7-8 h, | (+)-C1 (18%) |
| 10 | R-(+)-B1 | PhSeSePh, Selectfluor, Hexane:H$_2$O, rt, 7-8 h | (+)-C1 (22%) |
| 11 | R-(+)-B1 | PhSeSePh, K$_2$S$_2$O$_8$, ACN:H$_2$O, rt, 7-8 h | (+)-C1 (11%) |
| 12 | R-(+)-B1 | PhSeSePh, AgOTf, ACN:H$_2$O, rt, 7-8 h | (+)-C1 (13%) |
| 13 | R-(+)-B1 | PhSeBr, −30 to −35° C., ACN:H$_2$O, 24 h | (+)-C1 (41%) |
| 14 | R-(+)-B1 | PhSeBr, 0° C., THF:H$_2$O, 24 h | (+)-C1 (38%) |
| 15 | R-(+)-B1 | PhSeBr, Selectfluor −30 to −35° C., ACN:H$_2$O, 24 h | (+)-C1 (42%) |
| 16 | R-(+)-B1 | PhSeBr, AgOTf, −30 to −35° C., ACN:H$_2$O, 24 h | (+)-C1 (41%) |
| 17 | R-(+)-B1 | PhSeBr, −30 to −35° C., DCM:H$_2$O, 24 h | (+)-C1 (13%) |
| 18 | R-(+)-B1 | PhSeBr, −78° C., DCM:H$_2$O, 24 h, | (+)-C1 (6%) |
| 19 | R-(+)-B1 | PhSCl, −30° C., ACN:H$_2$O | (+)-C1 (19%) |

Preparation of (−)-1-methyl-2-(phenylselanyl)-4-(prop-1-en-2-yl)cyclohexan-1-ol (C2)

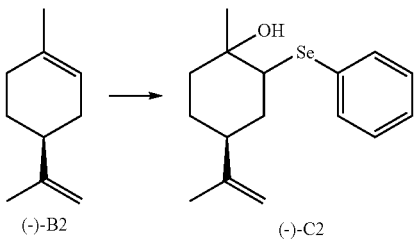

(−)-B2 → (−)-C2

Example 20: To a stirred solution of (S)-(−)-limonene (B2) (544 mg, 4.0 mmol) in ACN:H$_2$O (98:2, 6 ml) at −30 to −35° C. was added a solution of phenylselenyl bromide (256 mg, 1.0 mmol) in ACN and allowed to stir at the same temperature. The progress of the reaction was monitored by TLC. After completion of the reaction (approximately 24 h), the reaction mixture was poured in hypo solution and extracted with ethyl acetate (3 times). The organic layer was dried over Na$_2$SO$_4$ and concentrated in vacuum. The crude material was subjected to silica gel column chromatography R$_f$=0.4 EtOAc:Hexane (0.3-9.7) as an eluent to afford the title compound (−)-1-methyl-2-(phenylselanyl)-4-(prop-1-en-2-yl)cyclohexan-1-ol (C2) (39%) as a yellow oil. 1H NMR (400 MHz, CDCl$_3$): δ(ppm)=7.58 (dd, j=4 Hz, 2H), 7.27 (m, 3H), 4.71 (d, j=13.6 Hz, 2H), 3.44 (t, j=4 Hz, 1H), 2.33 (m, 1H), 2.21 (m, 1H), 1.85 (m, 2H), 1.68 (s, 3H), 1.64 (m, 3H), 1.41 (s, 3H), 1.26 (bs, 1H); $^{13}$C NMR (100 MHz, CDCl$_3$): δ(ppm)=149.03, 134.41, 130.55, 129.13, 127.39, 109.29, 72.59, 54.62, 39.54, 35.24, 33.70, 29.55, 26.24, 21.35; [α]$_D^{20}$=−138 (c=1.0, CHCl$_3$); LC-MS: (ESI+): m/z calcd for C$_{16}$H$_{22}$OSe 310.084; found 327.25.

TABLE 2

Reaction conditions for synthesis of
compound formula (−)-C2 from S-(−)-B2

| EXAMPLE | REACTANT | REAGENTS AND CONDITIONS | YIELD (%) |
|---|---|---|---|
| 21 | S-(−)-B2 | PhSeSePh, Selectfluor, rt ACN:H$_2$O, 7-8 h | (−)-C2 (35%) |

Preparation of (+) 4-(2-hydroxypropan-2-yl)-1-methyl-2-(phenylselanyl)cyclohexan-1-ol (C3)

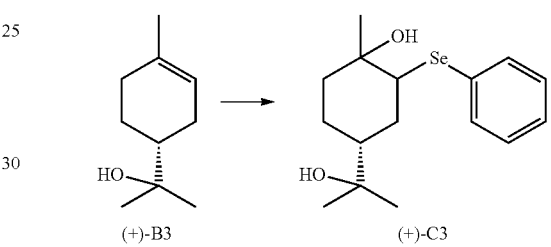

(+)-B3 → (+)-C3

Example 22: To a stirred solution of (+) α-terpineol (B3) (616 mg, 4.0 mmol) in ACN:H$_2$O (98:2, 6 ml) at −30 to −35° C. was added a solution of phenylselenyl bromide (256 mg, 1.0 mmol) in ACN and allowed to stir at the same temperature. The progress of the reaction was monitored by TLC. After completion of the reaction (approximately 24 h), the reaction mixture was poured in hypo solution and extracted with ethyl acetate (3 times). The organic layer was dried over Na$_2$SO$_4$ and concentrated in vacuum. The crude material was subjected to silica gel column chromatography R$_f$=0.5 EtOAc:Hexane (0.2-9.8) as a eluent to afford title compound (+) 4-(2-hydroxypropan-2-yl)-1-methyl-2-(phenylselanyl)cyclohexan-1-ol (C3) (268 mg, 82%) as a dark yellow oil. $^1$H NMR (400 MHz, CDCl$_3$): δ(ppm)=7.55 (dd, J=4 Hz, 2H), 7.25 (m, 3H), 3.54 (t, J=4 Hz, 1H), 2.63 (m, 1H), 2.24 (m, 1H), 1.65 (m, 2H), 1.55 (m, 3H), 1.25 (s, 3H), 1.23 (s, 3H), 1.12 (s, 3H). [α]$_D^{20}$=+79 (c=1.0, CHCl$_3$); LC-MS: (ESI+): m/z calcd for calcd C$_{16}$H$_{24}$O$_2$Se 327.094; found 293.25

TABLE 3

Reaction conditions for synthesis of
compound formula (+)-C3 from (+)-B3

| EXAMPLE | REACTANT | REAGENTS AND CONDITIONS | YIELD (%) |
|---|---|---|---|
| 23 | (+)-B3 | PhSeSePh, Selectfluor, ACN:H$_2$O, rt, 7-8 h | (+)-C3 (71%) |
| 24 | (+)-B3 | PhSeBr, −30 to −35° C., THF:H$_2$O, 24 h | (+)-C3 (76%) |

Preparation of (+)-2-(4-hydroxy-4-methyl-3-(phenylselanyl)cyclohexyl)propan-2-yl 2,2,2-trifluoroacetate (C4)

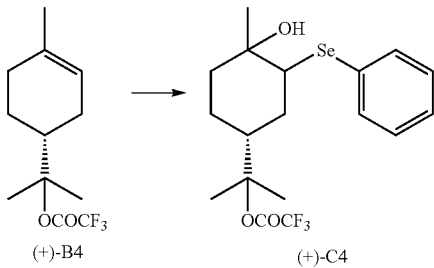

(+)-B4       (+)-C4

Example 25: To a stirred solution of 2-(4-methylcyclohex-3-en-1-yl)propan-2-yl 2,2,2-trifluoroacetate (B4) (1 g, 4.0 mmol) in ACN:H$_2$O (98:2, 6 ml) at −30 to −35° C. was added a solution of phenylselenyl bromide (256 mg, 1.0 mmol) in ACN and allowed to stir at the same temperature. The progress of the reaction was monitored by TLC. After completion of the reaction (approximately 24 h), the reaction mixture was poured in hypo solution and extracted with ethyl acetate (3 times). The organic layer was dried over Na$_2$SO$_4$ and concentrated in 3 vacuum. The crude material was subjected to silica gel column chromatography R$_f$=0.3 EtOAc:Hexane (0.4-9.6) as an eluent to afford the title compound (+)-2-(4-hydroxy-4-methyl-3-(phenylselanyl)cyclohexyl)propan-2-yl 2,2,2-trifluoroacetate (C4) (138.24 mg, 59%) as a yellow oil; $^1$H NMR (400 MHz, CDCl$_3$): δ(ppm)=7.58 (dd, J=4 Hz, 2H), 7.27 (m, 3H), 3.45 (d, J=4 Hz, 1H), 2.39 (m, 1H), 2.11 (m, 1H), 1.73 (m, 2H), 1.67 (m, 3H) 1.52 (s, 3H), 1.48 (s, 3H), 1.45 (s, 3H); [α]$_D^{20}$=+111 (c=1.0, CHCl$_3$); $^{19}$F NMR (376 MHz, CDCl$_3$): δ(ppm)=−75.65

TABLE 4

Reaction conditions for synthesis of compound formula (+)-C4 from (+)-B4

| EXAMPLE | REACTANT | REAGENTS AND CONDITIONS | YIELD (%) |
| --- | --- | --- | --- |
| 26 | (+)-B4 | PhSeSePh, Selectfluor, ACN:H$_2$O, rt, 7-8 h | (+)-C4 (37%) |

Preparation of 4-isopropyl-1-methyl-2-(phenylselanyl)cyclohexan-1-ol (C5)

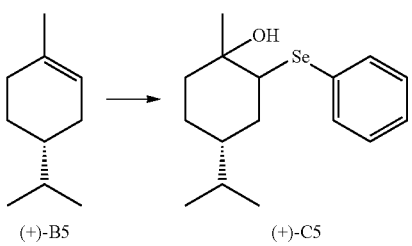

(+)-B5       (+)-C5

Example 27: To a stirred solution of (+)-4-isopropyl-1-methylcyclohex-1-ene (B5) (552 mg, 4.0 mmol) in ACN:H$_2$O (98:2, 6 ml) at −30 to −35° C. was added a solution of phenylselenyl bromide (256 mg, 1.0 mmol) in ACN and allowed to stir at the same temperature. The progress of the reaction was monitored by TLC. After completion of the reaction (approximately 24 h), the reaction mixture was poured in hypo solution and extracted with ethyl acetate (3 times). The organic layer was dried over Na$_2$SO$_4$ and concentrated in vacuum. The crude material was subjected to silica gel column chromatography R$_f$=0.5 EtOAc:Hexane (0.4-9.6) as an eluent to afford the title compound (+)-4-isopropyl-1-methyl-2-(phenylselanyl)cyclohexan-1-ol (C5) (138.24 mg, 86%) as a yellow oil. $^1$H NMR (400 MHz, CDCl$_3$): δ(ppm)=7.60 (dd, J=4 Hz, 2H), 7.28 (m, 3H), 3.44 (t, J=4 Hz, 1H), 2.03 (m, 1H), 1.81 (m, 3H), 1.57 (m, 3H), 1.40 (s, 3H), 0.88 (d, j=4 Hz, 3H), 0.83 (d, j=4 Hz, 3H)$^{13}$C NMR (100 MHz, CDCl$_3$): δ 134.53, 130.94, 129.31, 127.31, 72.68, 55.14, 39.22, 35.25, 32.37, 30.72, 29.10, 24.82, 20.14, 20.05; [α]$_D^{20}$=−101 (c=1.0, CHCl$_3$); LC-MS: (ESI+): m/z calcd for C$_{16}$H$_{24}$OSe; 295 [M-OH]$^+$.

TABLE 5

Reaction conditions for synthesis of compound formula (+)-C5 from (+)-B5

| EXAMPLE | REACTANT | REAGENTS AND CONDITIONS | YIELD (%) |
| --- | --- | --- | --- |
| 28 | (+)-B5 | PhSeBr, −30 to −35° C., ACN:H$_2$O, 24 h | (+)-C5 (86%) |

Step 2: Regeneration of the Double Bond by Elimination (C-D)

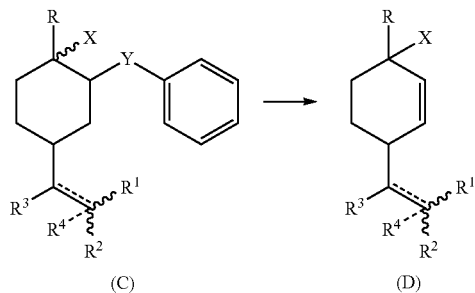

(C)       (D)

Preparation of (+)-1-methyl-4-(prop-1-en-2-yl)cyclohex-2-en-1-ol (D1)

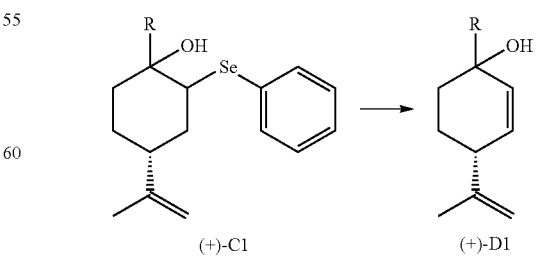

(+)-C1       (+)-D1

Example 29: The solution of (+)-1-methyl-2-(phenylselenyl)-4-(prop-1-en-2-yl)cyclohexan-1-ol (C1) (155 mg, 0.5 mmol) in THF (5 ml) was allowed to stir for 10 min. Then, Selectfluor (531 mg, 1.5 mmol) was added to the reaction. The reaction mixture was stirred for 9-10 h or until reactant gets consumed. The progress of reaction was monitored by TLC. The reaction mixture was poured in water and extracted with ethyl acetate. The crude material was subjected to silica gel column chromatography $R_f$=0.4 EtOAc:hexane (0.3-9.7) as an eluent to afford the title compound (+)-1-methyl-4-(prop-1-en-2-yl)cyclohex-2-en-1-ol (D1) (64.9 mg, 85%) as light yellow oil. $^1$H NMR (400 MHz, CDCl$_3$): δ(ppm)=5.71 (dd, 1H), 5.66 (dd, 1H), 4.78 (d, J=16 Hz, 1H), 4.75 (d, J=8 Hz, 1H), 2.66 (m, 1H), 1.80 (m, 2H), 1.74 (s, 3H), 1.59 (m, 1H), 1.49 (br, OH, 1H), 1.30 (s, 3H). $^{13}$C NMR (100 MHz, CDCl$_3$): δ(ppm)=148.125 (C-8), 134.13 (C-2), 132.20 (C-1), 110.74 (C-9), 67.41 (C-3), 43.34 (C-6), 36.77 (C-4), 29.70 (C-5), 27.10 (C-10), 20.81 (C-7); $[α]_D^{20}$Experimental=+146 (c=1.0, CHCl$_3$); literature=+53.8 (CHCl$_3$);

HRMS (ESI-TOF) m/z: [M-OH]-calcd for $C_{10}H_{16}O$; 152.120; found 135.15.

TABLE 6

Reaction conditions for synthesis of compound formula (+)-D1 from (+)-C1

| EXAMPLE | REACTANT | REAGENTS AND CONDITIONS | YIELD(%) |
|---|---|---|---|
| 30 | (+)-C1 | H$_2$O$_2$, THF, 0° to rt 7-8 h | (+)-D1(76%) |
| 31 | (+)-C1 | Oxone, THF, rt 14 h | (+)-D1(69%) |
| 32 | (+)-C1 | Selectfluor(1.5 mmol), THF, rt 10 h | (+)-D1(82%) |
| 33 | (+)-C1 | Selectfluor(0.5 mmol), THF, rt, 28 h | (+)-D1(76%) |
| 34 | (+)-C1 | Selectfluor(1.5 mmol), ACN, rt, 28 h | (+)-D1(76%) |
| 35 | (+)-C1 | N-fluorobenzenesulfonamide, THF, 9-10 h | (+)-D1(53%) |
| 36 | (+)-C1 | (Bis(trifluoroacetoxy)iodo-benzene), THF, 9-10 h | (+)-D1(24%) |

Preparation of (+)-1-methyl-2-(phenylselanyl)-4-(prop-1-en-2-yl)cyclohexan-1-ol (D2)

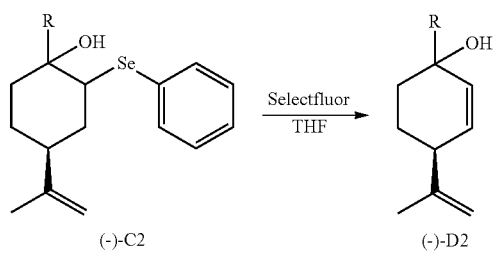

(-)-C2    (-)-D2

Example 37: The solution of (−)-1-methyl-2-(phenylselenyl)-4-(prop-1-en-2-yl)cyclohexan-1-ol (C2) (155 mg, 0.5 mmol) in THF (5 mL) was allowed to stir for 10 min. Then, (531 mg, 1.5 mmol) Selectfluor was added to the reaction. The reaction mixture was stirred for 9-10 h or until reactant gets consumed. The progress of reaction was monitored by TLC. The reaction mixture was poured in water and extracted with ethyl acetate. The crude material was subjected to silica gel column chromatography, $R_f$=0.4 EtOAc:hexane (0.3-9.7) as an eluent to afford the title compound (−)-1-methyl-4-(prop-1-en-2-yl)cyclohex-2-en-1-ol (D2) (81%) as light yellow oil. $^1$H NMR (400 MHz, CDCl$_3$): δ(ppm)=5.71 (dd, 1H), 5.66 (dd, 1H), 4.78 (d, J=16 Hz, 1H), 4.75 (d, J=8 Hz, 1H), 2.66 (m, 1H), 1.80 (m, 2H), 1.74 (s, 3H), 1.59 (m, 1H), 1.49 (br, OH, 1H), 1.30 (s, 3H); $^{13}$C NMR (100 MHz, CDCl$_3$): δ(ppm)=148.125 (C-8), 134.13 (C-2), 132.20 (C-1), 110.74 (C-9), 67.41 (C-3), 43.34 (C-6), 36.77 (C-4), 29.70 (C-5), 27.10 (C-10), 20.81 (C-7); $[α]_D^{20}$Experimental=−92 (c=1.0, CHCl$_3$); LC-MS: (ESI+): m/z calcd for $C_{10}H_{16}O$; 152.120; found 135.15.

Preparation of (+)-2-(4-hydroxy-4-methylcyclohex-2-en-1-yl)propan-2-yl 2,2,2-trifluoroacetate (D3)

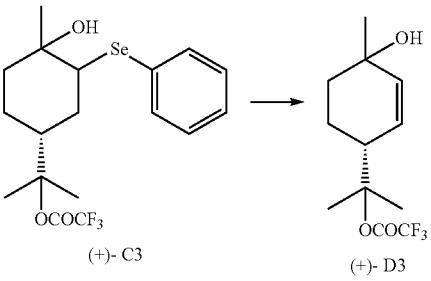

(+)- C3    (+)- D3

Example 38: The solution of (+)-2-(4-hydroxy-4-methyl-3-(phenylselanyl)cyclohexyl)propan-2-yl 2,2,2-trifluoroacetate (C3) (212 mg, 0.5 mmol) in THF (5 mL) was allowed to stir for 10 min. Then, (531 mg, 1.5 mmol) Selectfluor was added to the reaction. The reaction mixture was stirred for 9-10 h or until reactant gets consumed. The progress of reaction was monitored by TLC. The reaction mixture was poured in water and extracted with ethyl acetate. The crude material was subjected to silica gel column chromatography $R_f$=0.3 EtOAc:hexane (0.3-9.7) as an eluent to afford the title compound (+)-2-(4-hydroxy-4-methylcyclohex-2-en-1-yl)propan-2-yl 2,2,2-trifluoroacetate (D3) (79 mg, 59.3%) as light yellow oil. $^1$HNMR (400 MHz, CDCl$_3$): δ(ppm)=5.79 (m, 111), 5.67 (m, 111), 2.72 (s, 111), 2.49 (s, 111) 1.80 (m, 311), 1.57 (d, J=12 Hz, 3H), 1.52 (d, J=8 Hz, 3H) 1.29 (d, J=8 Hz, 3H). $^{19}$F NMR (376 MHz, CDCl$_3$): δ(ppm)=−75.65; $[α]_D^{20}$=+51 (c=1.0, CHCl$_3$)

TABLE 7

Reaction conditions for synthesis of compound formula (+)-D3 from (+)-C3

| EXAMPLE | REACTANT | REAGENTS AND CONDITIONS | YIELD (%) |
|---|---|---|---|
| 39 | (+)-C3 | H$_2$O$_2$, THF, 7-8 h | (+)-D3 (51.1%) |

Preparation of (+)-4-isopropyl-1-methylcyclohex-2-en-1-ol (D4)

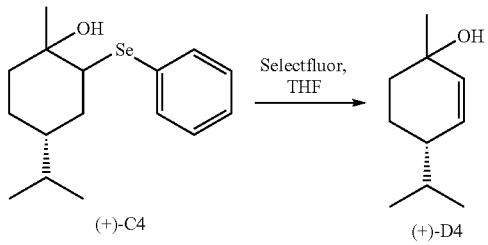 [SMILES: CC(C)[C@@H]1CCC(C)(O)C([Se]c2ccccc2)C1 ; CC(C)[C@H]1C=CC(C)(O)CC1]

Example 40: The solution of (+)-4-isopropyl-1-methyl-2-(phenylselanyl)cyclohexan-1-ol (C4) (156 mg, 0.5 mmol) in THF (5 mL) was allowed to stir for 10 min. Then, (531 mg, 1.5 mmol) Selectfluor was added to the reaction. The reaction mixture was stirred for 9-10 h or until reactant gets consumed. The progress of reaction was monitored by TLC. The reaction mixture was poured in water and extracted with ethyl acetate. The crude material was subjected to silica gel column chromatography $R_f$=0.5 EtOAc:hexane (0.3-9.7) as an eluent to afford the title compound (+)-4-isopropyl-1-methylcyclohex-2-en-1-ol (D4) (63%) as light yellow oil. $^1$H NMR (400 MHz, CDCl$_3$): δ(ppm)=$^1$H NMR (400 MHz, CDCl$_3$): δ 5.66 (m, 2H), 1.84 (m, 2H), 1.62 (m, 2H), 1.47 (m, 2H), 1.26 (s, 3H), 0.89 (m, 6H); $^{13}$C NMR (100 MHz, CDCl$_3$):133.64, 133.08, 67.59, 42.23, 37.36, 31.74, 29.74, 21.67, 19.65, 19.31; $[α]_D^{20}$Experimental=+48 (c=1.0, CHCl$_3$); LC-MS: (ESI+): m/z calcd for C$_{10}$H$_{18}$O; 154.136; found 137.136

TABLE 8

Reaction conditions for synthesis of compound formula (+)-D4 from (+)-C4

| EXAMPLE | REACTANT | REAGENTS AND CONDITIONS | YIELD (%) |
|---|---|---|---|
| 41 | (+)-C4 | H$_2$O$_2$, THF, 7-8 h | (+)-D4 (61%) |
| 42 | (+)-C4 | Selectfluor, toluene, 9-10 h | (+)-D4 (59%) |

Step 3: Condensation of Olivetol or Derivatives with Menthadienol or Derivatives to Prepare Cannabidiol or Derivatives

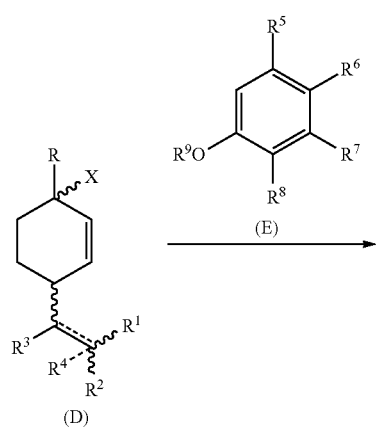

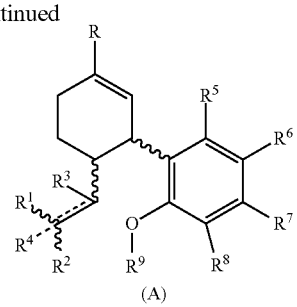

Preparation of (−)-5'-methyl-4-pentyl-2'-(prop-1-en-2-yl)-1',2',3',4'-tetrahydro-[1,1'-biphenyl]-2,6-diol (A1)

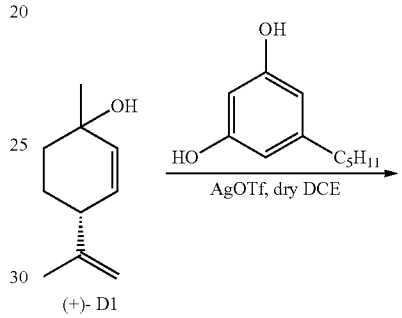

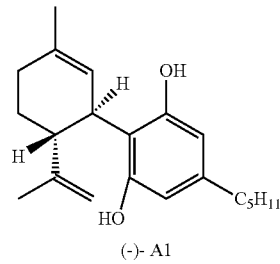

Example 43: To a solution of Silver bis(trifluoromethanesulfonyl)imide (AgNTf$_2$) (20 mol %) in anhydrous DCE was added (+)-1-methyl-4-(prop-1-en-2-yl)cyclohex-2-en-1-ol (D1) (76 mg, 0.5 mmol) in solution form using syringe. Then, olivetol (E1) (72 mg, 0.4 mmol) in solution form was added slowly to the reaction mixture. Then reaction was allowed to stir at room temperature under dark conditions until the completion of the reactant. The progress of reaction was monitored by TLC.

Reaction mixture was poured in water and extracted with EtOAc. The crude material was subjected to silica gel column chromatography $R_f$ 0.5 EtOAc/hexane (0.1:9.9) as an eluent to afford the title compound (−) 5'-methyl-4-pentyl-2'-(prop-1-en-2-yl)-1',2',3',4'-tetrahydro-[1,1'-biphenyl]-2,6-diol (A1) (67.18 mg, 43%) as a yellow oil $^1$H NMR (400 MHz, CDCl$_3$): δ(ppm)=6.22 (bs, 2H), 5.98 (bs, 1H, OH), 5.57 (s, 1H), 4.78 (bs, 1H, OH), 4.66 (s, 1H), 4.56 (s, 1H), 3.86 (dd, J=8 Hz, 1H), 2.43 (t, 2H), 2.38 (m, 1H), 2.22 (m, 1H), 2.10 (m, 1H), 1.83 (m, 2H), 1.79 (s, 3H), 1.66 (s, 3H), 1.56 (t, 3H), 1.30 (m, 4H), 0.88 (t, 3H); $^{13}$C NMR (100 MHz, CD$_3$OD): δ(ppm)=156.13, 148.90, 141.36, 133.20, 125.86, 114.61, 109.23, 107.02, 45.06, 36.13, 35.19, 31.23, 30.64, 30.31, 29.30, 22.29, 22.17, 18.17, 12.97; $[α]_D^{20}$=−43 (c=1.0, CHCl$_3$); LC-MS: (ESI+): m/z calcd for C$_{21}$H$_{31}$O$_2$; 314.225; found 315.2317.

Example 44: To a solution of silver triflate (20 mol %) in anhydrous DCE was added (+)-1-methyl-4-(prop-1-en-2-yl)cyclohex-2-en-1-ol (D1) (76 mg, 0.5 mmol) in solution form using syringe. Then, olivetol (E1) (72 mg, 0.4 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography $R_f$=0.5 EtOAc/hexane (0.1:9.9) as an eluent to afford the title compound (−) 5'-methyl-4-pentyl-2'-(prop-1-en-2-yl)-1',2',3',4'-tetrahydro-[1,1'-biphenyl]-2,6-diol (A1) (62.5 mg, 36%) as a yellow oil.

TABLE 9

Reaction conditions for synthesis of compound formula (−)-A1 from (+)-D1.

| EXAMPLE | REACTANT | REAGENTS AND CONDITIONS | YIELD (%) |
|---|---|---|---|
| 45 | (+)-D1 | Montmorillonite clay, dry DCE, rt, 8 h | (−)-A1 (34%) |
| 46 | (+)-D1 | AgOTf, dry DCE, phenanthrolene, rt, 8 h | (−)-A1 (22%) |
| 47 | (+)-D1 | AgOTf, dry DCE, pyridine, rt, 8 h | (−)-A1 (31%) |
| 48 | (+)-D1 | AgOTf, dry DCE, BINAP, rt, 8 h | (−)-A1 (18%) |
| 49 | (+)-D1 | AgOTf, dry DCE, phosphine, rt, 8 h | (−)-A1 (18%) |
| 50 | (+)-D1 | AgOTf, dry toluene, rt, 8 h | (−)-A1 (40%) |
| 51 | (+)-D1 | AgOTf, dry Benzene, rt, 8 h | (−)-A1 (40%) |

Preparation of (+Z)-5'-methyl-4-pentyl-2'-(prop-1-en-2-yl)-1',2',3',4'-tetrahydro-[1,1'-biphenyl]-2,6-diol (A2)

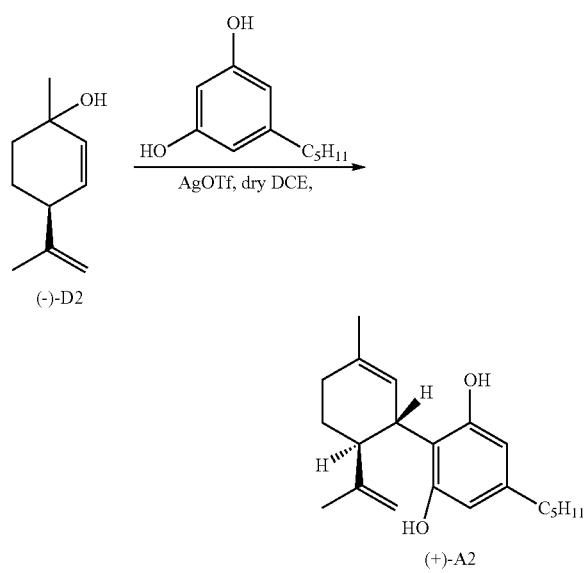

(+)-A2

Example 52 To a solution of silver triflate (20 mol %) in anhydrous DCE was added (−)-1-methyl-4-(prop-1-en-2-yl)cyclohex-2-en-1-ol (D2) (76 mg, 0.5 mmol) in solution form using syringe. Then, olivetol (72 mg, 0.4 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography $R_f$=0.5 EtOAc/hexane (0.1:9.9) as an eluent to afford the title compound (+)-5'-methyl-4-pentyl-2'-(prop-1-en-2-yl)-1',2',3',4'-tetrahydro-[1,1'-biphenyl]-2,6-diol (A2) (56.25 mg, 36%) as a yellow oil. $^1$H NMR (400 MHz, CDCl$_3$): δ(ppm)=6.22 (bs, 2H), 5.98 (bs, 1H, OH), 5.57 (s, 1H), 4.78 (bs, 1H, OH), 4.66 (s, 1H), 4.56 (s, 1H), 3.86 (dd, J=8 Hz, 1H), 2.43 (t, 2H), 2.38 (m, 1H), 2.22 (m, 1H), 2.10 (m, 1H), 1.83 (m, 2H), 1.79 (s, 3H), 1.66 (s, 3H), 1.56 (t, 3H), 1.30 (m, 4H), 0.88 (t, 3H); $^{13}$C NMR (100 MHz, CDCl$_3$): δ(ppm)=161.11 (2'C and 6'C), 149.37 (8 C), 142.99 (4-'C), 140.00 (3-C), 124.08 (2C), 113.87 (1'C), 110.92 (3'C and 5'C), 46.20 (6 C), 37.24 (1C), 35.50 (1" C), 32.51 (4 C), 30.61 (3" C), 30.42 (2" C), 28.44 (5C), 23.66 (7C), 22.55 (4" C), 20.47 (9 C), 14.03 (5" C); $[α]_D^{20}$=+21 (c=1.0, CHCl$_3$); LC-MS: (ESI+): m/z calcd for $C_{21}H_{31}O_2$; 314.225; found 315.2317.

TABLE 10

Reaction conditions for synthesis of compound formula (+)-A1 from (−)-D1.

| EXAMPLE | REACTANT | REAGENTS AND CONDITIONS | YIELD (%) |
|---|---|---|---|
| 53 | (−)-D2 | AgOTf, dry toluene | (+)-A2 (34%) |

Preparation of (−)-2-((1R,2R)-2',6'-dihydroxy-5-methyl-4'-pentyl-1,2,3,4-tetrahydro-[1,1'-biphenyl]-2-yl)propan-2-yl 2,2,2-trifluoroacetate (A3)

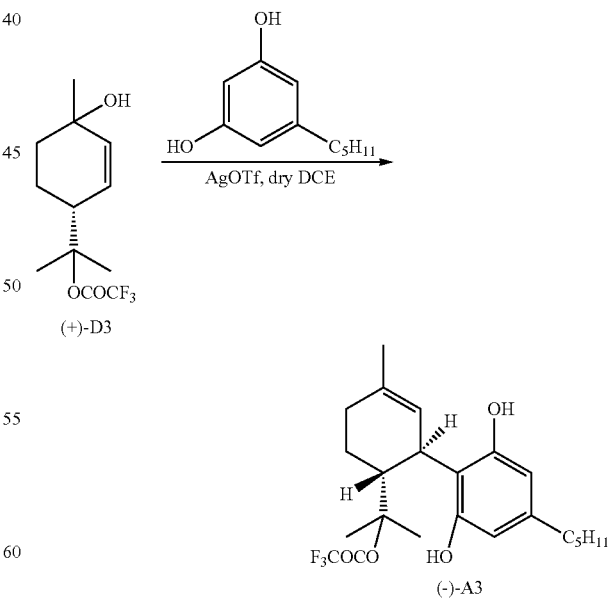

(−)-A3

Example 54: To a solution of silver triflate (20 mol %) in anhydrous DCE was added 2-(4-hydroxy-4-methylcyclohex-2-en-1-yl)propan-2-yl 2,2,2-trifluoroacetate (D3) (133 mg, 0.5 mmol) in solution form using syringe. Then, olivetol (180 mg, 1 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography $R_f$ 0.4 EtOAc/hexane (0.2:9.9) as an eluent to afford the title compound (−)-2-((1R,2R)-2',6'-dihydroxy-5-methyl-4'-pentyl-1,2,3,4-tetrahydro-[1,1'-biphenyl]-2-yl)propan-2-yl 2,2,2-trifluoroacetate (A3) (81 mg, 41%) as a yellow oil. $^1$H NMR (400 MHz, CDCl$_3$): δ(ppm)=6.22 (bs, 2H), 5.98 (bs, 1H, OH), 5.57 (s, 1H), 4.78 (bs, 1H, OH), 4.66 (s, 1H), 4.56 (s, 1H), 3.86 (dd, J=8 Hz, 1H), 2.43 (t, 2H), 2.38 (m, 1H), 2.22 (m, 1H), 2.10 (m, 1H), 1.83 (m, 2H), 1.79 (s, 3H), 1.66 (s, 3H), 1.56 (t, 3H), 1.30 (m, 4H), 0.88 (t, 3H); $^{19}$F NMR (376 MHz, CDCl$_3$): δ(ppm)=−75.65; $^{13}$C NMR (100 MHz, CD$_3$OD): δ(ppm)=156.13, 148.90, 141.36, 133.20, 125.86, 114.61, 109.23, 107.02, 45.06, 36.13, 35.19, 31.23, 30.64, 30.31, 29.30, 22.29, 22.17, 18.17, 12.97; $[α]_D^{20}$=−43 (c=1.0, CHCl$_3$).

TABLE 11

Reaction conditions for synthesis of compound formula (−)-A3 from (+)-D3

| EXAMPLE | REACTANT | REAGENTS AND CONDITIONS | YIELD (%) |
|---|---|---|---|
| 55 | (+)-D3 | AgOTf, dry toluene | (−)-A3 (40%) |

Preparation of (−)-(1'S,2'S)-2'-isopropyl-5'-methyl-4-pentyl-1',2',3',4'-tetrahydro-[1,1'-biphenyl]-2,6-diol (A4)

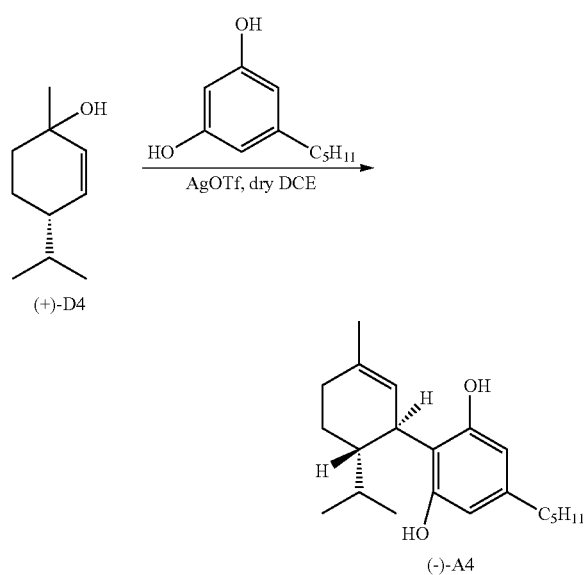

(+)-D4

(−)-A4

Example 56: To a solution of silver triflate (20 mol %) in anhydrous DCE was added (+) 4-isopropyl-1-methylcyclohex-2-en-1-ol (D4) (76 mg, 0.5 mmol) in solution form using syringe. Then, olivetol (E1) (72 mg, 0.4 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography $R_f$ 0.5 EtOAc/hexane (0.1:9.9) as an eluent to afford the title compound (−)-(1'S,2'S)-2'-isopropyl-5'-methyl-4-pentyl-1',2',3',4'-tetrahydro-[1,1'-biphenyl]-2,6-diol (A4) (39%) as a yellow oil. $^1$H NMR (400 MHz, CDCl$_3$): δ(ppm)=6.22 (bs, 2H), 5.98 (bs, 1H, OH), 5.57 (s, 1H), 4.78 (bs, 1H, OH), 3.86 (dd, J=8 Hz, 1H), 2.43 (t, 2H), 2.38 (m, 1H), 2.22 (m, 1H), 2.10 (m, 1H), 1.83 (m, 2H), 1.79 (s, 3H), 1.66 (s, 6H), 1.56 (t, 3H), 1.30 (m, 4H), 0.88 (t, 3H); $[α]_D^{20}$=−48 (c=1.0, CHCl$_3$); LC-MS: (ESI+): m/z for C$_{19}$H$_{26}$O$_3$; 317.240 [M+H]$^+$.

TABLE 12

Reaction conditions for synthesis of compound formula (−)-A4 form (+)-D4

| EXAMPLE | REACTANT | REAGENTS AND CONDITIONS | YIELD (%) |
|---|---|---|---|
| 57 | (+)-D4 | AgOTf, dry toluene | (−)-A4 (38%) |

Preparation of (−)-5'-methyl-2'-(prop-1-en-2-yl)-4-propoxy-1',2',3',4'-tetrahydro-[1,1'-biphenyl]-2,6-diol (A5)

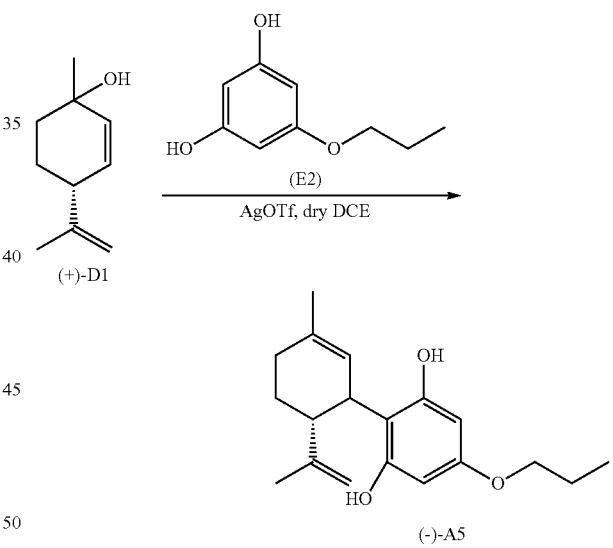

(+)-D1

(−)-A5

Example 58—To a solution of silver triflate (20 mol %) in anhydrous DCE was added (+) 1-methyl-4-(prop-1-en-2-yl) cyclohex-2-en-1-ol (D1) (76 mg, 0.5 mmol) in solution form using syringe. Then, 5-propoxybenzene-1,3-diol (E2) (100 mg, 0.6 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography $R_f$ 0.4 EtOAc/hexane (0.1:9.9) as an eluent to afford the title compound (−)-5'-methyl-2'-(prop-1-en-2-yl)-4-propoxy-1',2',3',4'-tetrahydro-[1,1'-biphenyl]-2,6-diol (A5) (62.2 mg, 41.05%) as a yellow oil. $^1$H NMR (400 MHz, CDCl$_3$): δ(ppm)=6.04 (bs, 2H), 5.59 (s, 1H), 4.74 (s, 1H), 4.62 (s, 1H), 3.86 (t, 2H), 3.69 (m, 1H), 2.38 (m, 1H), 2.22 (m, 1H), 2.10 (m, 1H), 1.83 (m, 2H), 1.79 (s, 3H), 1.66 (s, 3H), 1.30 (m, 2H), 1.06 (t, 3H); $[\alpha]_D^{20}=-21$ (c=1.0, CHCl$_3$); LC-MS: (ESI+): m/z calcd for C$_{19}$H$_{26}$O$_3$; 303.40.

Preparation of (−)-4-(dodecyloxy)-5'-methyl-2'-(prop-1-en-2-yl)-1',2',3',4'-tetrahydro-[1,1'-biphenyl]-2,6-diol

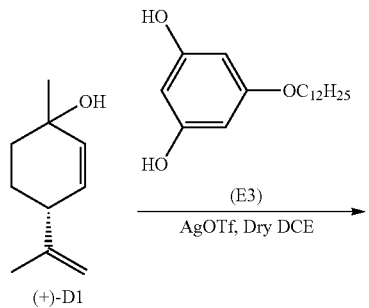

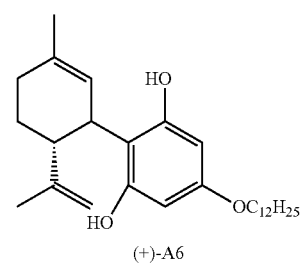

Example 59—To a solution of silver triflate (20 mol %) in anhydrous DCE was added (+) 1-methyl-4-(prop-1-en-2-yl) cyclohex-2-en-1-ol (D1) (76 mg, 0.5 mmol) in solution form using syringe. Then, 5-(dodecyloxy)benzene-1,3-diol (E3) (118 mg, 0.4 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography R$_f$ 0.4 EtOAc/hexane (0.1:9.9) as an eluent to afford the title compound (−)-5'-methyl-2'-(prop-1-en-2-yl)-4-propoxy-1',2',3',4'-tetrahydro-[1,1'-biphenyl]-2,6-diol (A6) (78 mg, 36.4%) as a yellow oil. $^1$HNMR (400 MHz, CDCl$_3$) δ(ppm)=5.96 (s, 2H), 5.48 (s, 1H), 4.61 (s, 1H), 4.51 (s, 1H), 3.78 (t, 3H), 3.71 (m, 1H), 2.28 (m, 1H), 2.21-1.95 (m, 2H), 1.72 (s, 3H), 1.68-1.62 (m, 2H), 1.58 (s, 3H), 1.19 (s, 20H), 0.81 (s, 3H). $^{13}$C NMR (101 MHz, CDCl$_3$) δ(ppm)=159.03, 149.54, 140.21, 111.17, 108.98, 67.78, 46.35, 31.93, 30.41, 29.62, 29.30 12.4 28.44, 26.05, 23.04, 20.76, 14.44. LC-MS: (ESI+): m/z calcd for C$_{21}$H$_{31}$O$_2$; 428.33; found 429.40.

Preparation of (−)-4,5'-dimethyl-2'-(prop-1-en-2-yl)-1',2',3',4'-tetrahydro-[1,1'-biphenyl]-2,6-diol (Cannabidiorcinol) (A7)

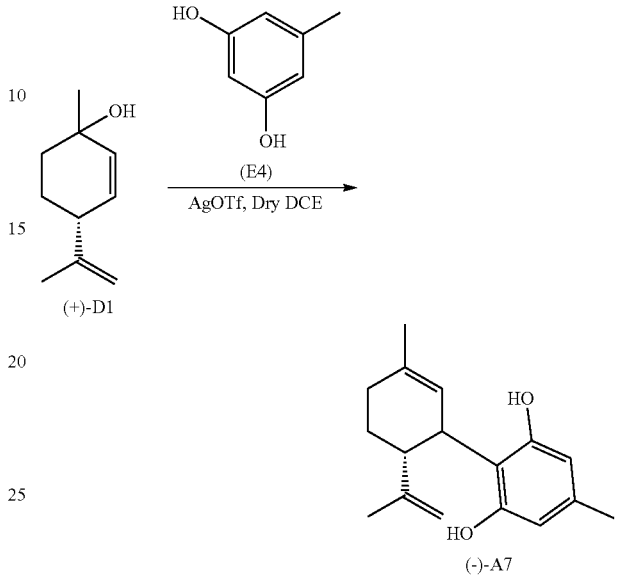

Example 60—To a solution of silver triflate (20 mol %) in anhydrous DCE was added (+) 1-methyl-4-(prop-1-en-2-yl) cyclohex-2-en-1-ol (D1) (76 mg, 0.5 mmol) in solution form using syringe. Then, Orcinol (E4) (50 mg, 0.4 mmol) in solution form was added slowly to the reaction mixture. Then reaction was allowed to stir at room temperature under dark conditions until the completion of the reactant. The progress of reaction was monitored by TLC. Reaction mixture was poured in water and extracted with EtOAc. The crude material was subjected to silica gel column chromatography R$_f$0.4 EtOAc/hexane (0.1:9.9) as an eluent to afford the title compound (−)-4,5'-dimethyl-2'-(prop-1-en-2-yl)-1', 2',3',4'-tetrahydro-[1,1'-biphenyl]-2,6-diol (Cannabidiorcinol) (A7) (41 mg, 39%)) as a yellow oil. 1H NMR (400 MHz, CDCl$_3$) δ(ppm)=6.15 (d, 2H), 5.89 (bs, OH), 5.48 (s, 1H), 4.59 (s, 1H), 4.49 (s, 1H), 3.78 (d, 1H), 2.33 (m, 1H), 2.14 (s, 1H), 2.01 (m, 1H), 1.72-1.67 (m, 3H), 1.59 (s, 3H), 1.51 (s, 3H). 13C NMR (101 MHz, CDCl$_3$) δ(ppm)=149.32, 137.95, 113.89, 110.90, 46.02, 30.27, 21.35, 20.31.

Advantages of the Present Invention:

The present invention deals with a novel process development for the production of a (+) or (−) Cannabidiol and related compounds thereof. The (+) or (−) cannabidiol and related compounds thereof can be prepared via three steps sequence bi-functionalization of (+) or (−) limonene or limonene derivative thereof, elimination to (+) or (−) menthadienol or derivatives thereof, and metal triflate or acid or heteroacid catalyzed condensation of (+) or (−) menthadienol or menthadienol derivatives with olivetol or olivetol derivatives thereof. The processes of the present disclosure provide a number of advantages over current methods. The main advantage of the present disclosure are i) inexpensive and commercially available starting materials, ii) accessibility of the (+) or (−) cannabidiol or derivatives, iii) high selectivity in condensation reaction, and iv) high overall yield.

We claim:
1. A process for the preparation of cannabidiol compound of formula (A)

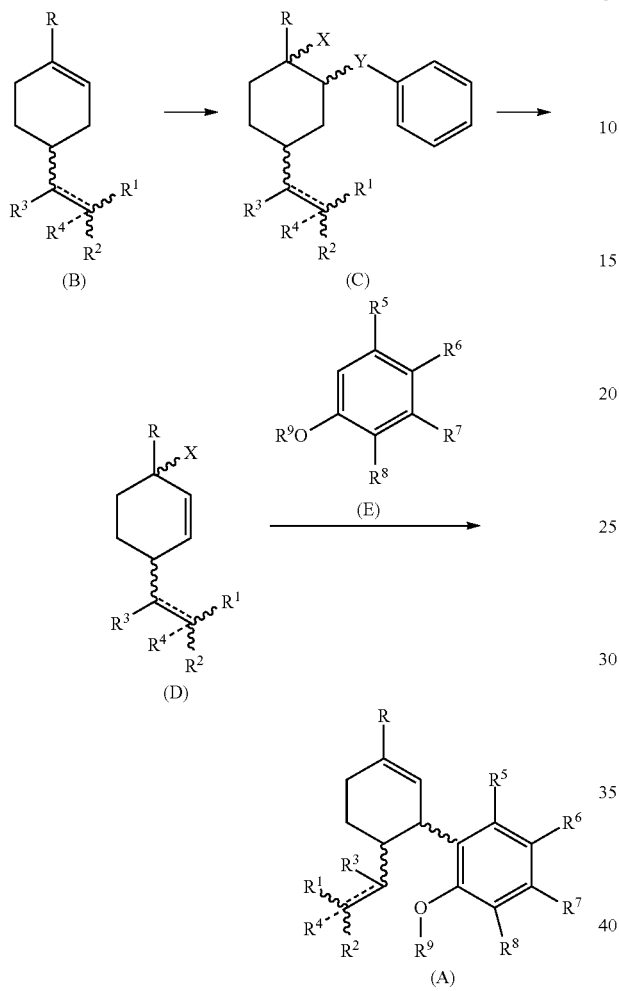

comprising the steps of:
(a) contacting a compound of formula (B) with a reagent selected from PhSeBr, PhSeCl, PhSCl, PhSBr, PhSSPh/AgOTf, PhSSPh/N-Chloromethyl-N'-fluorotriethylenediammonium bis(tetrafluoroborate), PhSeSePh/AgOTf, or PhSeSePh/N-Chloromethyl-N'-fluorotriethylenediammonium bis(tetrafluoroborate),
in the presence of a solvent or a mixture of solvents selected from $H_2O$, tetrahydrofuran, dioxane, acetonitrile, chlorobenzene, dichloroethane, acetone, hexane, dichloromethane, chloroform, ethyl acetate, and toluene; and with stirring for a time period in the range of 0.1 h-48 h and at a temperature in the range of −80° C. to 60° C., whereby a compound of formula (C) is produced;
(b) contacting the compound of formula (C) with an oxidant selected from mCPBA, Oxone, DDQ, CAN, N-hydroxy succinamide, t-Butylhydroperoxide, N-Chloromethyl-N'-fluorotriethylenediammonium bis (tetrafluoroborate), Hydrogen peroxide, BIAB, NFSI, TMSOTf, PyF-BF4, PyF-OTf, TMPyF-OTf, and PIFA, in the presence of a solvent or a mixture of solvents selected from $H_2O$, tetrahydrofuran, dioxane, acetonitrile, chlorobenzene, dichloroethane, acetone, hexane, dichloromethane, chloroform, ethyl acetate, and toluene; and with stirring the for a time period in the range of 0.1 to 48 hours at a temperature in the range of −40° C. to 60° C., whereby a compound of formula (D) is produced;
(c) contacting the compound of formula (D) with a compound of formula (E) in the presence of
(i) a metal triflate selected from AgOTf, $Ni(OTf)_2$, $Hg(OTf)_2$, LiOTf, $Bi(OTf)_3$, $Ln(OTf)_3$, and $Ac(OTf)_x$, optionally in the presence of a ligand selected from bipyridyl, substituted bipyridyl phenanthrolene, substituted phenanthrolene, pyridine, substituted pyridine, BINAP, QINAP, PINAP, $Ph_3P$; or
(ii) a heterogeneous acid selected from mixed metal oxides, $SiO_2$—$SO_3H/COFe_2O_4$, $SiO_2$—Pr—$SO_3H$, zeolites, zeotype materials, OMR-[C4HMTA] [$SO_3H$], MPD-$SO_3$H-IL, MeAPSO, MeAPO, SAPO, $ALPO_4$, Natrolite, ZSM-5, H-ZSM-5, periodic mesoporous organosilicas (PMOs), mesoporous silicas (PMSs), $H_3PW_{12}O_{40}$, $H_4SiW_{12}O_{40}$, $Cs_2HPW_{12}O_{40}$, $HPW/ZrO_2$, $HPW/Nb_2O_5$, Montmorillonite, pyrophyllite, Talc, Vermiculite, Sauconite, Saponite, Nontronite, Kaolinite, Chlorite, Illite, SAPO-34, Zirconium phosphates or sulphates, cation/anion exchange resins, amberlyst, and amberlite;
in the presence of a solvent or mixture of solvents selected from tetrahydrofuran, dioxane, acetonitrile, chlorobenzene, dichloroethane, acetone, hexane, dichloromethane, chloroform, ethyl acetate, and toluene; and with stirring for time period in the range of 0.1 to 48 hours at a temperature in the range of −40° C. to 60° C.;
wherein
R is independently selected from H, OH, alkyl, alkenyl, alkynyl, and cycloalkyl;
$R_1$, $R_2$, $R_3$ and $R_4$ are independently selected from H, OH, alkyl, alkenyl, alkynyl, acyl, acyloxy, and cycloalkyl;
X is independently selected from OH, H, heteroaryl, Cl, Br, I, OTf, OTs, and phosphinyl;
Y is independently selected from S and Se;
wherein, each ------ represents a single or double bond; provided that both ------ groups are not double bonds, and wherein denoted, dash marks indicate the points of attachment;
wherein, ⌇⌇ represents a single bond, above the plane or below the plane or both above the plane or both below the plane or one is above the plane and one is below the plane.
2. The process as claimed in claim 1, wherein
the compound of formula (C) is selected from:
a) (+)-1-methyl-2-(phenylselanyl)-4-(prop-1-en-2-yl)cyclohexan-1-ol
b) (−)-1-methyl-2-(phenylselanyl)-4-(prop-1-en-2-yl)cyclohexan-1-ol
c) 4-(2-hydroxypropan-2-yl)-1-methyl-2-(phenylselanyl)cyclohexan-1-ol
d) (+)-2-(4-hydroxy-4-methyl-3-(phenylselanyl)cyclohexyl) propan-2-yl 2,2,2-trifluoroacetate, and
e) 4-isopropyl-1-methyl-2-(phenylselanyl)cyclohexan-1-ol;
the compound of formula (D) is selected from:
f) (+)-1-methyl-4-(prop-1-en-2-yl)cyclohex-2-en-1-ol
g) (+)-1-methyl-2-(phenylselanyl)-4-(prop-1-en-2-yl)cyclohexan-1-ol (D2)

h) (+)-2-(4-hydroxy-4-methylcyclohex-2-en-1-yl) propan-2-yl 2,2,2-trifluoroacetate, and
i) (+)-4-isopropyl-1-methylcyclohex-2-en-1-ol; and the compound of formula (A) is selected from:

j) (−)-5'-methyl-4-pentyl-2'-(prop-1-en-2-yl)-1',2',3',4'-tetrahydro-[1,1'-biphenyl]-2,6-diol
k) (+Z)-5'-methyl-4-pentyl-2'-(prop-1-en-2-yl)-1',2',3',4'-tetrahydro-[1,1'-biphenyl]-2,6-diol l) (−)-2-((1R,2R)-2',6'-dihydroxy-5-methyl-4'-pentyl-1,2,3,4-tetrahydro-[1,1'-biphenyl]-2-yl) propan-2-yl 2,2,2-trifluoroacetate
m) (−)-(1'S,2'S)-2'-isopropyl-5'-methyl-4-pentyl-1',2',3',4'-tetrahydro-[1,1'-biphenyl]-2,6-diol
n) (−)-5'-methyl-2'-(prop-1-en-2-yl)-4-propoxy-1',2',3',4'-tetrahydro-[1,1'-biphenyl]-2,6-diol o)(−)-4-(dodecyloxy)-5'-methyl-2'-(prop-1-en-2-yl)-1',2',3',4'-tetrahydro-[1,1'-biphenyl]-2,6-diol p)(−)-4,5'-dimethyl-2'-(prop-1-en-2-yl)-1',2',3',4'-tetrahydro-[1,1'-biphenyl]-2,6-diol.

3. The process according to claim 1, wherein the metal triflate is AgOTf, and the heterogeneous acid is montmorillonite clay.

4. The process according to claim 1, wherein in step (a), the contacting is carried out in the further presence of an oxidant selected from mCPBA, Oxone, DDQ, CAN, N-Hydroxy succinamide, t-Butylhydroperoxide, N-Chloromethyl-N'-fluorotriethylenediammonium bis(tetrafluoroborate), Hydrogen peroxide, BIAB, NFSI, TMSOTf, PyF-BF$_4$, PyF-OTf, and TMPyF-OTf.

5. The process according to claim 1, wherein in step (b), the oxidant is N-Chloromethyl-N'-fluorotriethylenediammonium bis(tetrafluoroborate).

* * * * *